(12) United States Patent
Eifler et al.

(10) Patent No.: US 7,975,692 B2
(45) Date of Patent: Jul. 12, 2011

(54) RESPIRATORY DEVICE

(75) Inventors: Martin Eifler, Glückstadt (DE); Arnold Frerichs, Buxtehude (DE)

(73) Assignee: Weinmann Geräte für Medizin GmbH & Co. KG, Hamburg (DE)

( * ) Notice: Subject to any disclaimer, the term of this patent is extended or adjusted under 35 U.S.C. 154(b) by 1149 days.

(21) Appl. No.: 11/660,176

(22) PCT Filed: Jul. 7, 2005

(86) PCT No.: PCT/DE2005/001202
§ 371 (c)(1),
(2), (4) Date: Feb. 14, 2007

(87) PCT Pub. No.: WO2006/024249
PCT Pub. Date: Mar. 9, 2006

(65) Prior Publication Data
US 2008/0168991 A1 Jul. 17, 2008

(30) Foreign Application Priority Data

Sep. 3, 2004 (DE) .......................... 10 2004 043 208
May 27, 2005 (DE) .......................... 10 2005 024 254

(51) Int. Cl.
*A62B 18/02* (2006.01)
(52) U.S. Cl. ......... 128/205.25; 128/206.21; 128/204.18; 128/207.13
(58) Field of Classification Search ............. 128/205.25, 128/205.24, 207.11, 206.21, 206.23–28, 128/207.18, 207.13, 207.12, 204.18, 204.27, 204.24, 207.16
See application file for complete search history.

(56) References Cited

U.S. PATENT DOCUMENTS

| | | | | |
|---|---|---|---|---|
| 4,811,730 A * | 3/1989 | Milano | ................... | 128/203.11 |
| 5,438,981 A * | 8/1995 | Starr et al. | ............... | 128/205.24 |
| 5,687,715 A * | 11/1997 | Landis et al. | ............ | 128/207.18 |
| 2002/0023649 A1* | 2/2002 | Gunaratnam et al. | ... | 128/205.25 |
| 2002/0174868 A1* | 11/2002 | Kwok et al. | ............. | 128/205.25 |
| 2003/0084904 A1 | 5/2003 | Gunaratnam | | |
| 2003/0164170 A1* | 9/2003 | Drew et al. | ............. | 128/204.18 |
| 2003/0172936 A1* | 9/2003 | Wilkie et al. | ............ | 128/207.18 |
| 2004/0065327 A1* | 4/2004 | Gradon et al. | ........... | 128/205.25 |
| 2004/0065330 A1 | 4/2004 | Landis | | |
| 2004/0094157 A1 | 5/2004 | Dantanarayana | | |
| 2005/0072428 A1* | 4/2005 | Ho et al. | ................... | 128/205.25 |
| 2006/0090760 A1* | 5/2006 | Gradon et al. | ........... | 128/206.27 |
| 2006/0278233 A1* | 12/2006 | McAuley et al. | ........ | 128/206.12 |
| 2007/0137647 A1* | 6/2007 | Dampney | ................. | 128/204.18 |

FOREIGN PATENT DOCUMENTS
EP 1 099 452 5/2001
* cited by examiner

*Primary Examiner* — Justine R Yu
*Assistant Examiner* — Colin Stuart
(74) *Attorney, Agent, or Firm* — Lucas & Mercanti, LLP; Klaus P. Stoffel

(57) ABSTRACT

A device for artificial respiration, including a front support (3) which is connected to a respiratory mask (1) that includes a connection for the respiratory tube (4), a front support is coupled to the respiratory mask by a distancing element (2) and at least one cavity (11) is arranged in the region of the distancing element, the cavity leading into an inner chamber (12).

29 Claims, 27 Drawing Sheets

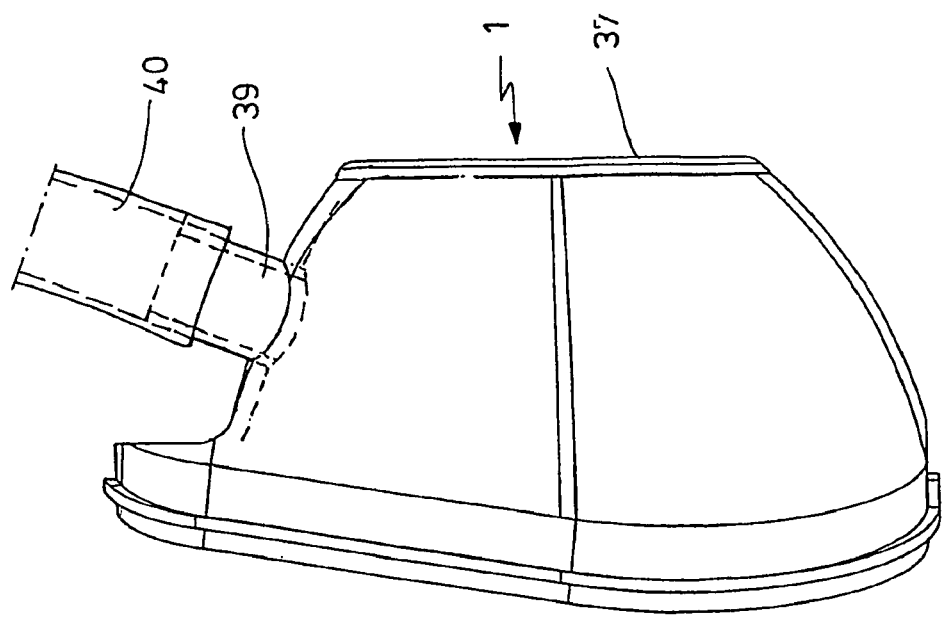
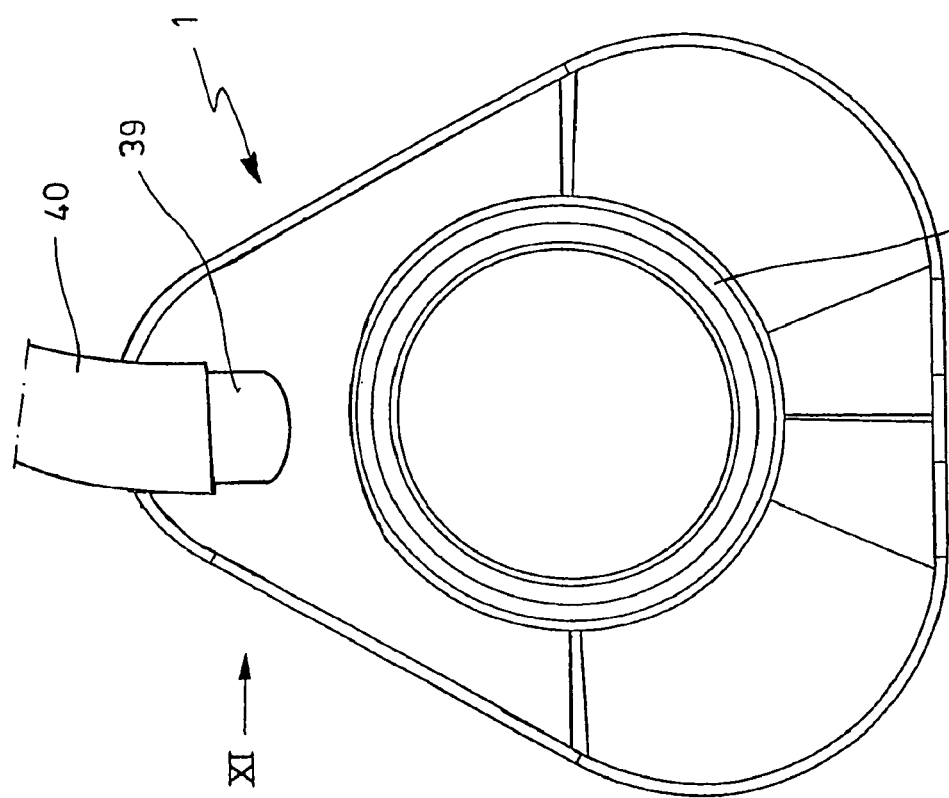

RESPIRATORY DEVICE

BACKGROUND OF THE INVENTION

The invention concerns a ventilator, which has a forehead support connected with a ventilator mask, where the ventilator mask is provided with a connection for a ventilator hose, and where the forehead support is coupled with the ventilator mask by a spacing element.

A typical use of devices of this type is in connection with respiratory air supply systems used in CPAP therapy (CPAP=continuous positive airway pressure). They can also be used in bilevel ventilation, APAP ventilation, home ventilation, and hospital emergency ventilation.

Typically, an expiratory element, which diverts the patient's exhaled respiratory gas to the environment, is installed in the area of the ventilator hose just in front of the connection of the ventilator hose with the ventilator mask. Especially when the ventilator mask is used during nighttime hours, previously known expiratory elements still cannot meet all requirements with respect to comfort of use. When the patient is in a reclining position, the expiratory elements are often positioned in front of his throat or chest, which causes the air to flow towards the patient. This kind of air flow causes cooling and possibly drying of the skin exposed to the air flow. Therefore, the patients catch cold relatively often unless suitable countermeasures are taken, but patients also often find these countermeasures unpleasant.

SUMMARY OF THE INVENTION

The objective of the present invention is to design a device of the aforementioned type in such a way that exhaled air does not flow in the patient's direction.

In accordance with the invention, this objective is achieved by providing the spacing element with at least one cavity, which opens into an interior space of the ventilator mask.

By designing the spacing element with a cavity, it is possible to divert the respiratory gas exhaled by the patient in such a way that the gas does not flow against the patient's throat or chest. User comfort can be greatly improved in this way, and the risk of colds can be reduced.

The discharge of respiratory gas in the vicinity of the forehead support is assisted if the cavity opens into an interior space of the forehead support.

A possibility for the discharge of the respiratory gas consists in the fact that the spacing element has at least one discharge opening.

In particular, it is advantageous if the discharge opening faces away from the patient.

In another design variant, the forehead support is provided with at least one discharge opening.

When the respiratory gas is discharged through the forehead support, it is also advantageous for the discharge opening to face away from the patient.

Optimum elimination of carbon dioxide from the respiratory gas is supported by providing at least certain areas of the ventilator mask with a double-walled construction.

To support favorable flow guidance, it is provided that the body of the ventilator mask and an inner shell together bound a flow channel that opens into the cavity.

It is also conducive to uniform flow guidance for a coupling part for the ventilator hose to extend through the flow channel into the region of the interior space of the ventilator mask.

To guarantee that an intended ventilation pressure is maintained, it is proposed that an adjustable baffle be installed in the area of at least one of the discharge openings to produce a discharge resistance that can be preset.

Simple manipulation of the baffle can be realized with a sliding baffle.

The use of a rotatable baffle has also been found to be advantageous.

In another design variant, a membrane element is installed in the area of at least one of the discharge openings.

In addition, it is proposed that a slotted silicone insert be installed in the area of at least one of the discharge openings.

Discharge of exhaled respiratory gas as a function of the given position of the ventilator mask or the patient can be realized by installing a movable closure element in the area of at least one of the discharge openings.

In particular, it has been found to be advantageous for the closure element to be installed in a way that allows its position to be varied.

Position-dependent positioning of the closure element can be realized in a simple way by designing the closure element as a ball.

In accordance with another embodiment, the closure element is designed as a baffle.

To ensure that a predetermined therapeutic pressure is maintained, at least one throttle element can be installed in the spacing element to control the flow resistance.

Another possible means of directing the flow of respiratory gas is the installation of a movable discharge nozzle in the vicinity of at least one discharge opening.

Modular adaptability to different practical requirements can be realized through the use of interchangeable throttle modules in the spacing element.

In accordance with a simplified embodiment, it is proposed that the ventilator mask have at least one discharge opening that faces away from the patient.

The discharge of exhaled respiratory gas away from the patient is promoted by the discharge of the respiratory gas with the use of an expiratory hose.

A compact design can be realized by arranging the cavity inside the spacing element.

A modular system design can be realized if the cavity is located in a flow guide element outside the spacing element.

If the ventilator mask consists of at least two detachably connected components, this also contributes to simple configurability.

Assembly and disassembly operations are assisted if the two or more components are connected with one another by a manually releasable locking mechanism.

Well-defined flow paths for avoiding a constriction of respiratory gas flowing in and respiratory gas flowing out can be realized if at least one of the components is hollow and is designed for removing exhaled air.

In addition, the production of well-defined flow paths is supported by the use of a ventilator mask that preferably consists of at least three detachably connected components, of which at least two components are connected with one another by a manually releasable locking mechanism, and one of the components is designed for removing exhaled air, and the other component is designed for supplying fresh respiratory gas.

Separate flow paths are also realized if at least two of the components have an internal cavity, and one of the components is designed basically for removing exhaled air, and the other component is designed basically for supplying fresh respiratory gas.

Furthermore, it is proposed that at least two of the components have an internal cavity and that in at least one operating state, a higher average concentration of carbon dioxide be present in one of the hollow components than in the area of the other component.

A general design principle for realizing separate flow paths is described by a ventilator mask which has at least three interconnected openings and in which at least one of the openings opens into a cavity, and at least one of the openings is designed basically for removing exhaled air, and the other opening is designed basically for supplying fresh respiratory gas.

In a typical design, at least one of the openings opens into a cavity, and this opening is designed basically for removing exhaled air in a direction radially away from the body of the mask, and the other opening is designed basically for supplying fresh respiratory gas.

It is also proposed that at least one of the openings have an internal cavity, and that this opening be designed essentially for removing exhaled air above the eye level of the patient, while the other opening be designed essentially for supplying fresh respiratory gas.

Comfort of use is further enhanced if at least one of the openings opens into a cavity, and this opening is designed basically for discharging exhaled air to a point far from the patient's face, while the other opening is designed basically for supplying fresh respiratory gas.

In addition, it is proposed that a discharge channel for creating an exhalation system extend along at least certain parts of the forehead support.

Discharge of respiratory gas in a direction away from the patient can also be realized by providing a flow path into the ventilator mask for an air flow coming from a compressed gas source and by providing a discharge channel for discharging the exhaled air, such that the discharge channel extends at an angle of 45° to 135° relative to a plane that is defined by the perpendicular of the inlet for the respiratory gas supply.

In addition, it has been found to be advantageous in a general way for a cavity located in the forehead support to be connected by at least one connecting passage with an interior space of the ventilator mask and at least one discharge opening.

Specific embodiments of the invention are illustrated in the accompanying schematic drawings.

BRIEF DESCRIPTION OF THE DRAWING

FIG. 10 shows another embodiment with a discharge opening in the ventilator mask, in which a discharge hose is placed on a discharge connector.

FIG. 11 shows a side view in viewing direction XI in FIG. 10.

DETAILED DESCRIPTION OF THE INVENTION

Figure 1:
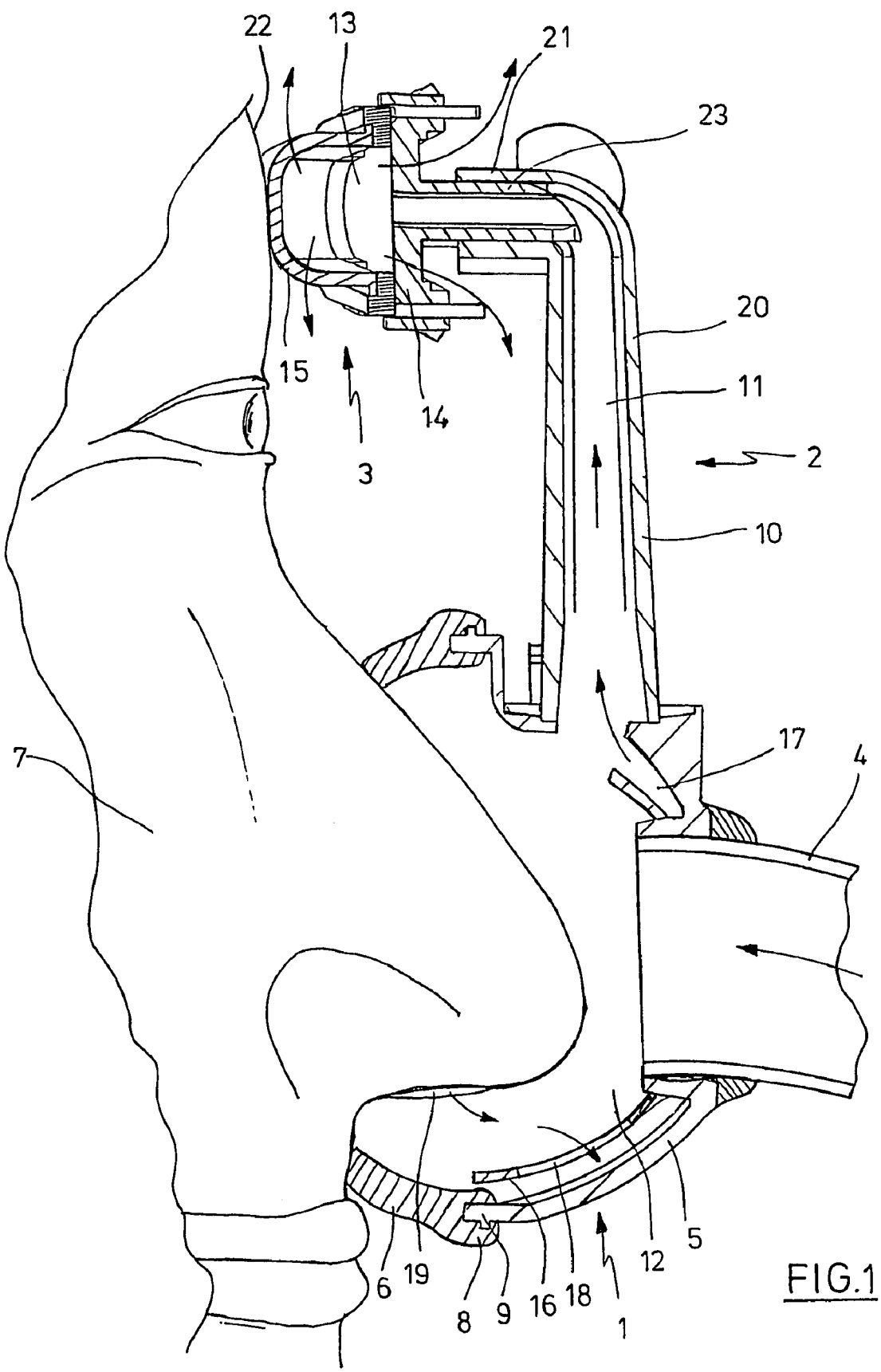
FIG. 1 shows a longitudinal section through a ventilator mask with a forehead support. The mask is positioned on the patient's head, and respiratory gas is discharged through the forehead support.

FIG. 1 shows an embodiment in which a ventilator mask 1 is coupled with a forehead support 3 by a spacing element 2. A ventilator hose 4 opens into the ventilator mask 1.

The ventilator mask 1 consists of a mask body 5 made of a strong material and a sealing element 6, which rests against the face of a patient 7 and is connected by a profile 8 with a mating profile 9 of the body 5 of the mask.

The spacing element 2 has an outer wall 10 that bounds a cavity 11, which opens into an interior space 12 of the ventilator mask 1. In the embodiment shown in FIG. 1, the cavity 11 opens into an interior space 13 of the forehead support in its expanded area facing away from the ventilator mask 1. The forehead support 3 consists essentially of a body 14 and a cushion 15.

The ventilator hose 4 is preferably rotatably supported in the body 5 of the mask. In the embodiment of FIG. 1, the body 5 of the mask is equipped with an inner shell 16, which provides a double-walled construction. A flow channel 17 extends between the inner shell 16 and the mask body 5 and is connected with the interior space 12 of the ventilator mask 1 by at least one opening 18 in the inner shell 16. The opening 18 is preferably located near the nostrils 19 of the patient 7.

Furthermore, the flow channel 17 is arranged in such a way that it ends in the vicinity of the opening of the cavity 11 into the interior space 12 of the ventilator mask 1. In this way, the respiratory gas exhaled by the patient is carried through the opening 18 and the flow channel 17 and into the area of the cavity 11. This design largely prevents any mixing of fresh respiratory gas from the ventilator hose 4 and exhaled respiratory gas. Ventilation effectiveness can be increased in this way.

The spacing element 2 has an angled design in the embodiment according to FIG. 1. A base segment 20 extends essentially vertically, and an end segment 21 extends more or less perpendicularly to the base segment 20 in the direction of the forehead 22 of the patient 7. The body 14 of the forehead support 3 has a mounting device 23 that fits into the end segment 21 and allows transverse positioning of the forehead support 3 relative to the spacing element 2.

The principal flow directions of the respiratory gas are indicated in FIG. 1 by flow arrows. In particular, the drawing shows that a large portion of the exhaled respiratory gas is discharged from the forehead support 3 in a direction away from the patient 7. Optimum discharge of the respiratory gas can be achieved by suitable predetermination of the discharge openings in the area of the forehead support 3.

Figure 2:
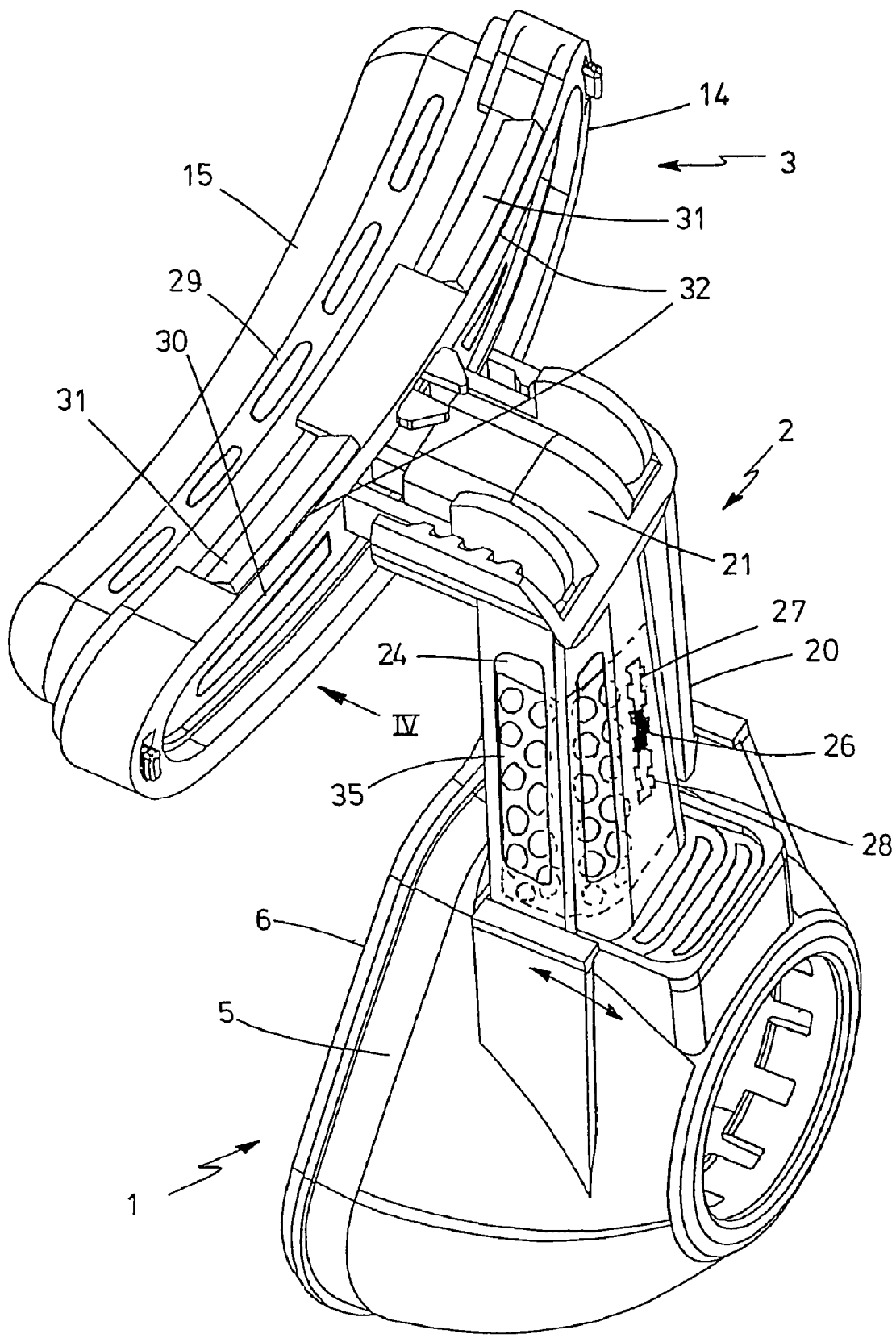
FIG. 2 shows a perspective view of a ventilator mask with a forehead support and adjustable discharge openings in the area of a spacing element of the forehead support.

FIG. 2 shows an embodiment in which discharge openings 24 are placed in the area of the spacing element 2. The discharge openings 24 can be at least partially covered by a baffle 25, which is installed in such a way that it can be positioned by an adjusting element 26. By adjusting the baffle 25, a suitable discharge resistance can be preset to prevent gas from flowing directly from the ventilator hose 4 to the discharge openings 24. The baffle 25 thus ensures that the required ventilation pressure can develop in the ventilator mask 1. The adjusting element 26 can be designed, for example, as a slide that can be positioned along a groove 27. Adequate positioning reliability can be provided by catches 28.

The embodiment in FIG. 2 also provides for the placement of discharge openings 29 in the area of the cushion 15 of the forehead support 3. In the embodiment according to FIG. 2, discharge openings 30 are also provided in the area of the body 14 of the forehead support 13.

In the embodiment according to FIG. 2, additional discharge openings 32 of the forehead support 3 are located in an upper region of the body 14, and the size of the discharge openings 32 can be preset by closure elements 31 that can be turned.

Figure 3:
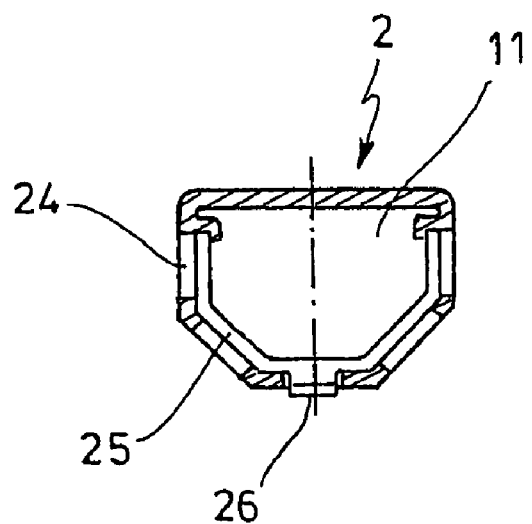
FIG. 3 shows a cross section through the spacing element of the forehead support.

FIG. 3 shows a cross section through the spacing element 2. It is apparent that the displaceable baffle 25 is located in a region of transition from the cavity 11 into the discharge openings 24.

Figure 4:
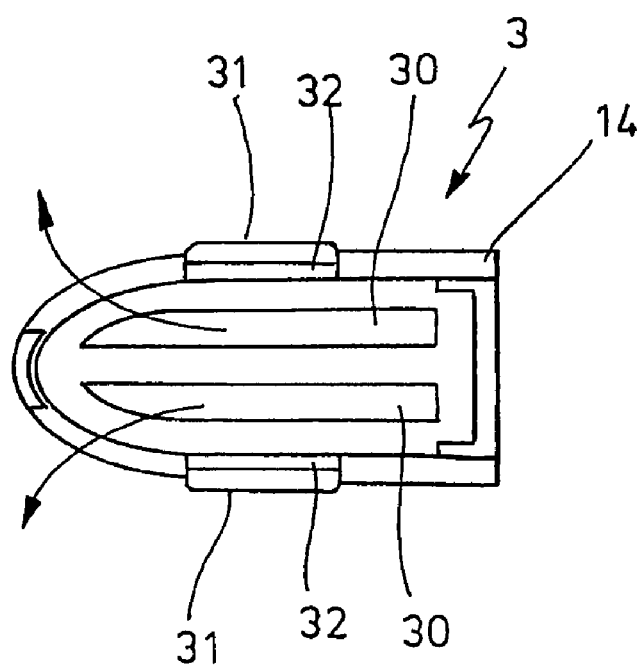
FIG. 4 shows a partial view of the forehead support in viewing direction IV in FIG. 2.

FIG. 4 is a side view that again shows the location of the discharge openings 30, 32 in the area of the forehead support 3 and the positioning of the closure elements 31. It is apparent that the corresponding discharge openings 32 can be placed at both the top and the bottom of the forehead support 3.

Figure 5:
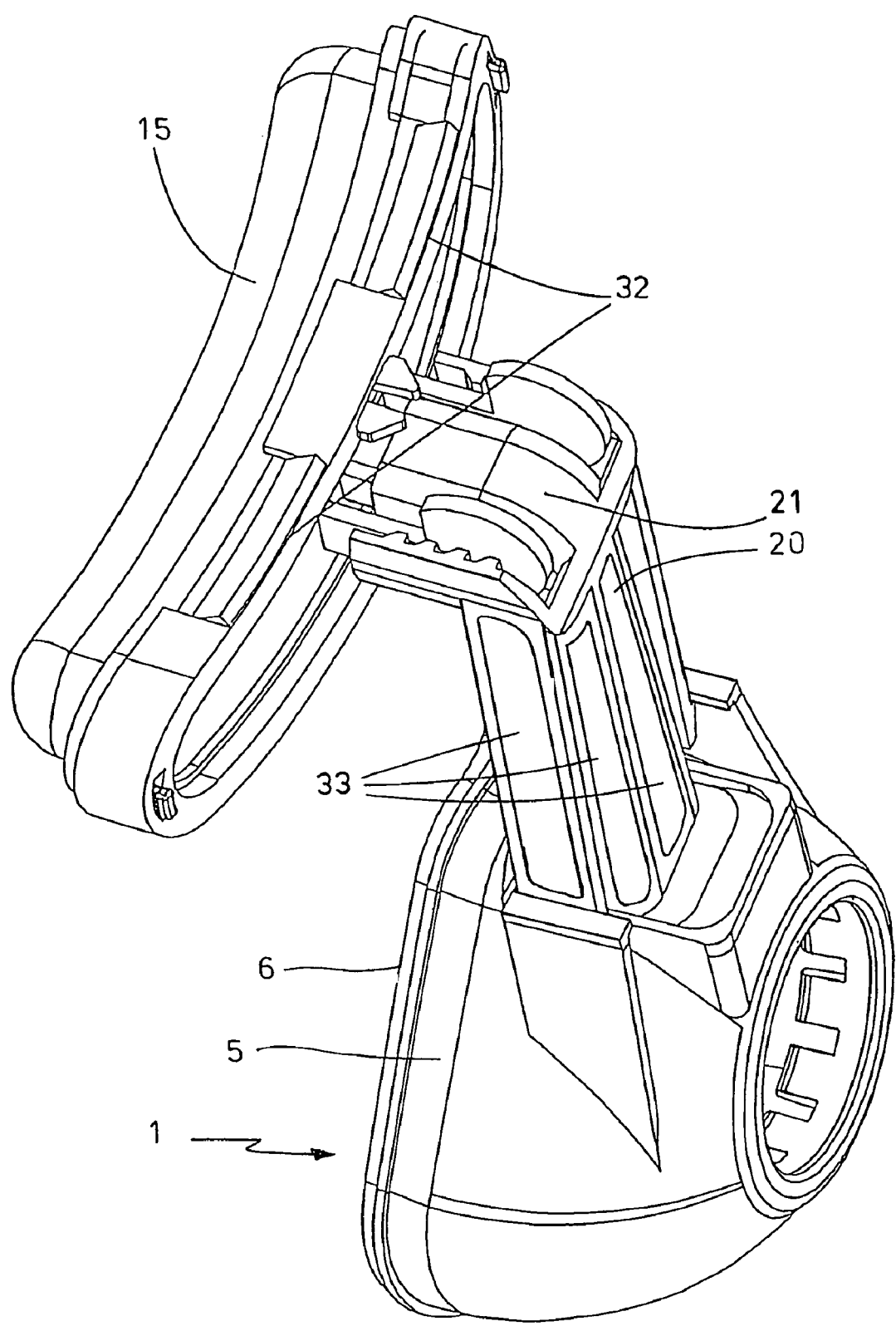
FIG. 5 shows an embodiment that employs membrane inserts.

FIG. 5 shows an embodiment in which membrane elements 33 are arranged in the area of the discharge openings 24 of the spacing element 2 to produce a suitable discharge resistance. The membranes can also be provided with moisture-retaining properties to prevent increased drying out of the patient by the ventilation. Similar membrane elements 33 can also be placed in the area of the discharge openings 29, 30, 32 of the forehead support 3.

Figure 6:
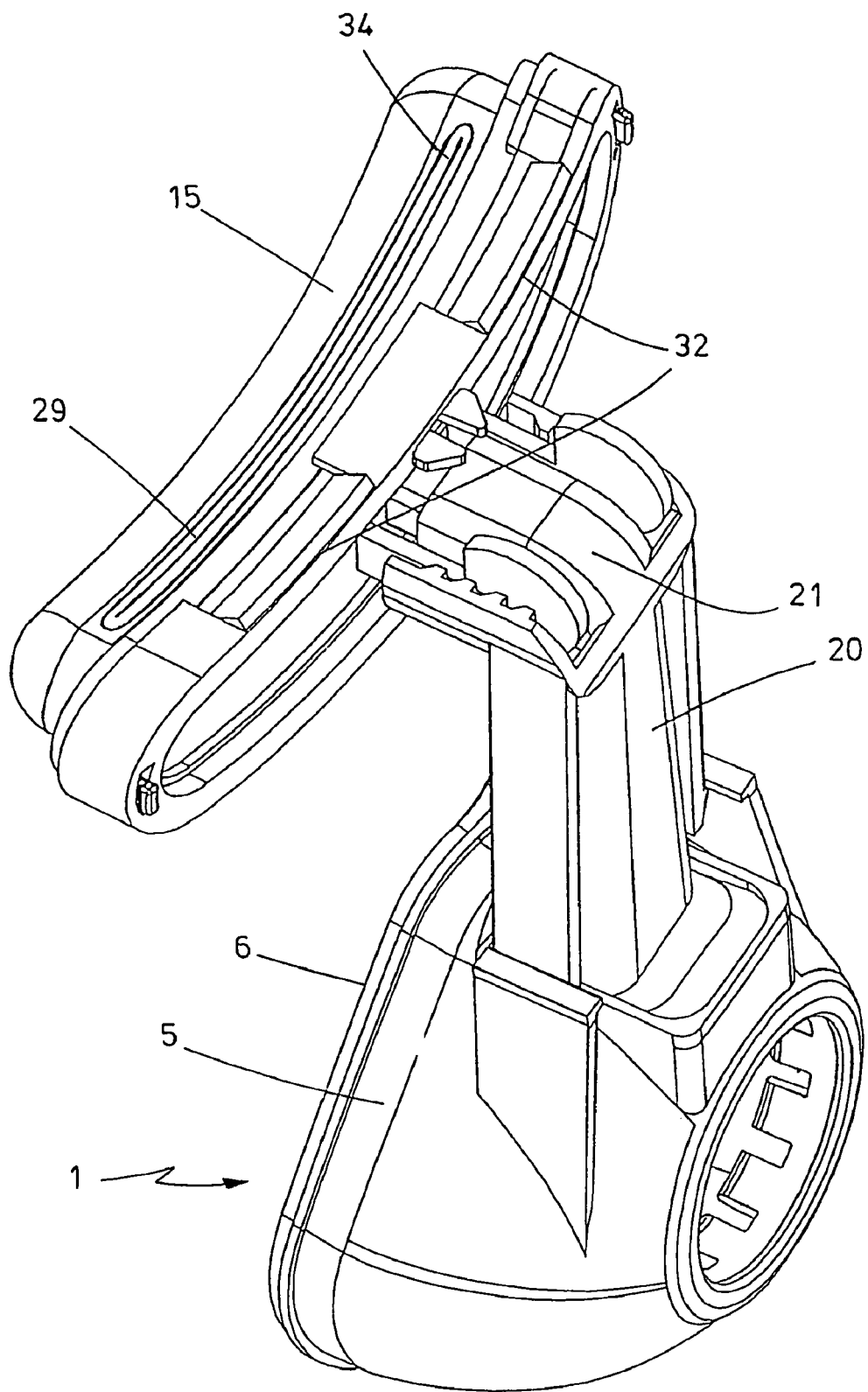
FIG. 6 shows an embodiment that employs slotted silicone inserts.

In the embodiment in FIG. 6, slotted silicone inserts 34 are placed in the area of the cushion 15 to provide discharge openings 29. The silicone inserts 34 can be placed both at the top and the bottom of the forehead support 3.

Figure 7:
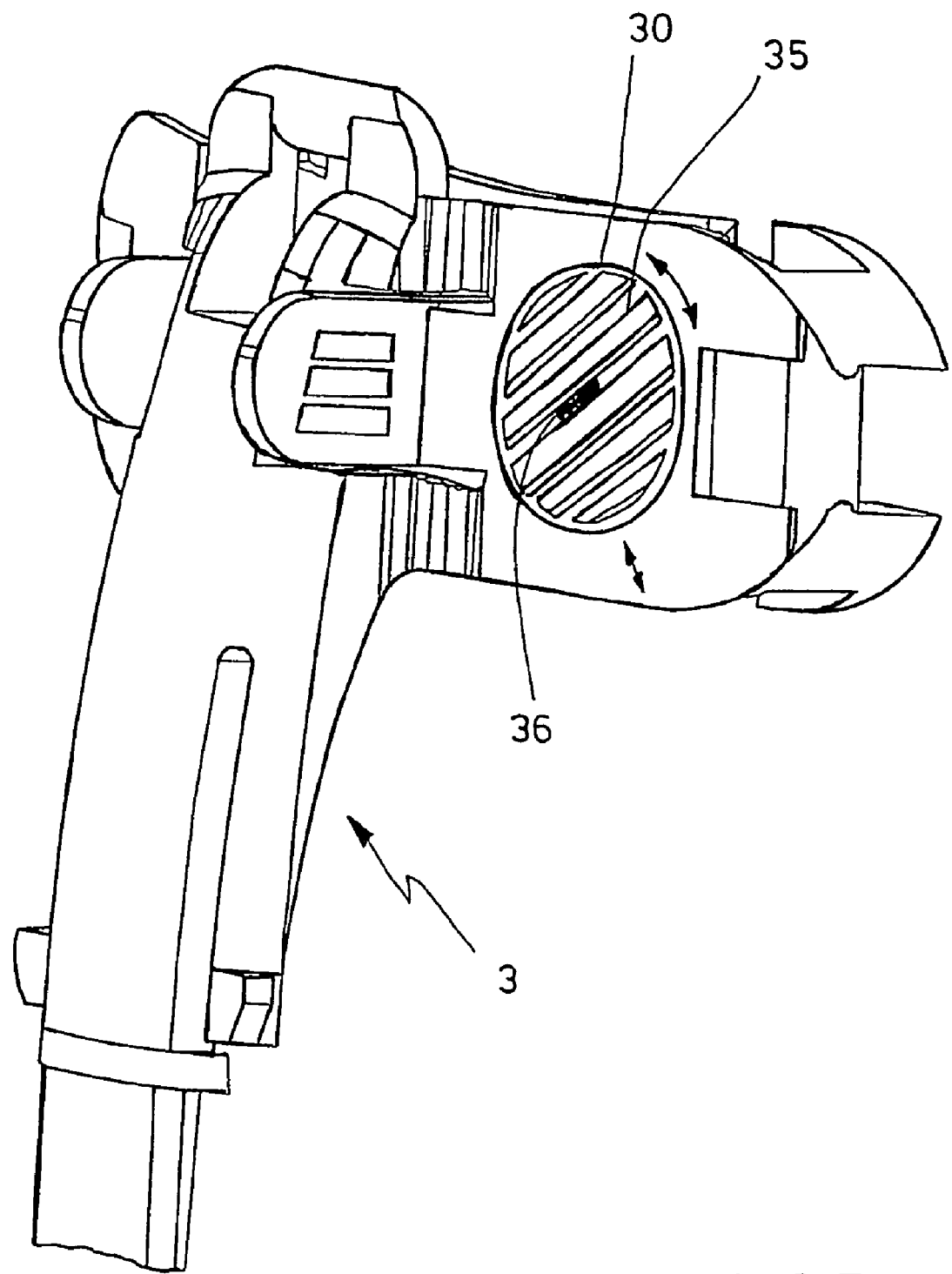
FIG. 7 shows an embodiment with adjustable discharge openings.

In the embodiment in FIG. 7, at least one discharge opening 30 that can be closed to a predeterminable extent by a baffle 35 is located in the area of the forehead support 3. The baffle 35 can be rotated by means of an operating element 36 and provides an adjustable state of opening of the discharge opening 30. The baffle 35 can be provided, for example, with holes, slots, or adjustable expiratory flaps.

Figure 8:
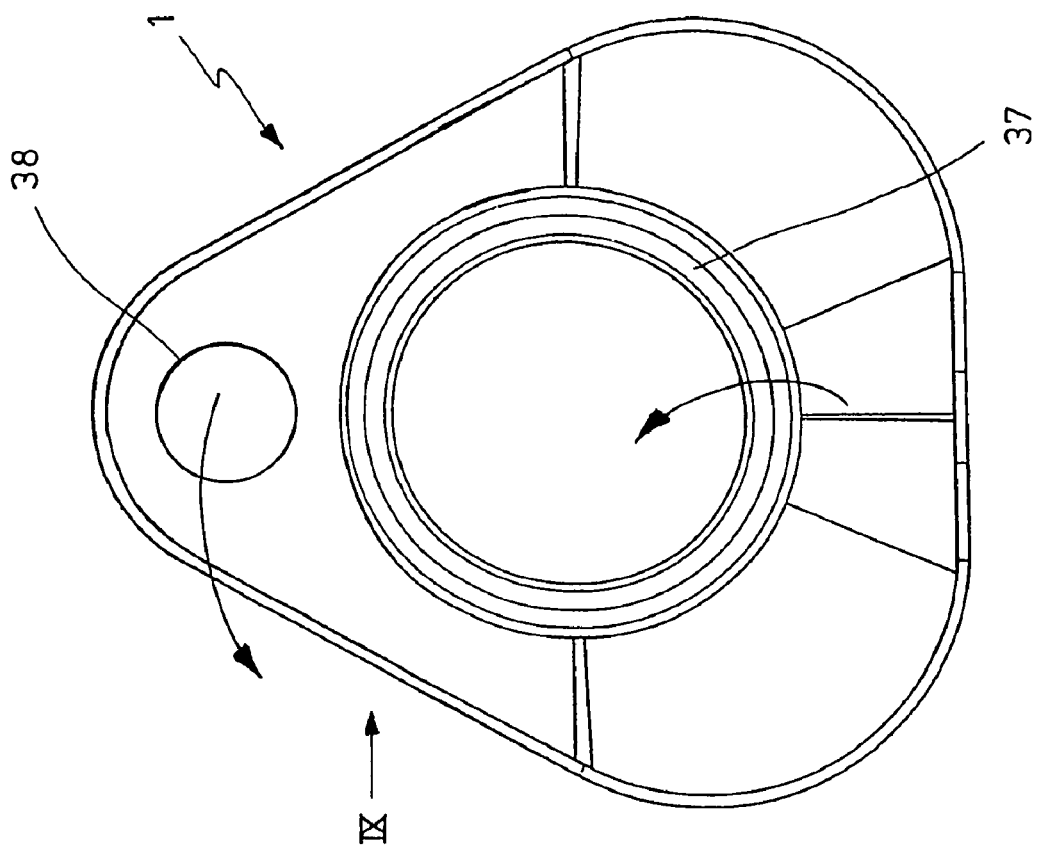
FIG. 8 shows a ventilator mask with a discharge opening for the elimination of carbon dioxide.

FIG. 8 shows an embodiment that can be used for optimum discharge of exhaled respiratory gas without the use of a forehead support 3. To this end, in its operating state, the ventilator mask 1 has a discharge opening 38 above a coupling part 37 for the ventilator hose, which is not shown in FIG. 8. The discharge opening 38 conducts the exhaled respiratory gas in a direction away from the patient.

Figure 9:
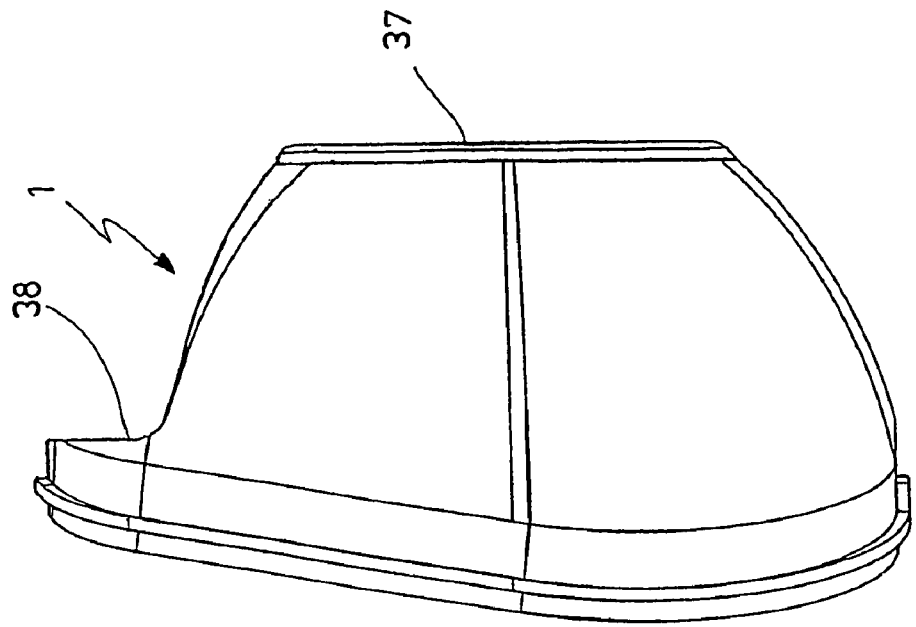
FIG. 9 shows a side view in viewing direction IX in FIG. 8.

FIG. 9 illustrates that the discharge opening 38 is preferably located in a flattened region of the ventilator mask 1. Respiratory gas is supplied exclusively through the coupling part 37 and is discharged through the discharge opening 38. This has been found to provide optimum elimination of carbon dioxide.

The embodiment according to FIG. 10 and FIG. 11 is functionally similar to the embodiment in FIGS. 8 and 9. However, instead of a simple discharge opening 38, this embodiment has a discharge connector 39, to which an expiratory hose 40 is connected. The use of the expiratory hose 40 makes it possible for the exhaled respiratory air to be discharged at almost any desired predetermined point, so that patient comfort can be optimized in this respect.

Figure 12:
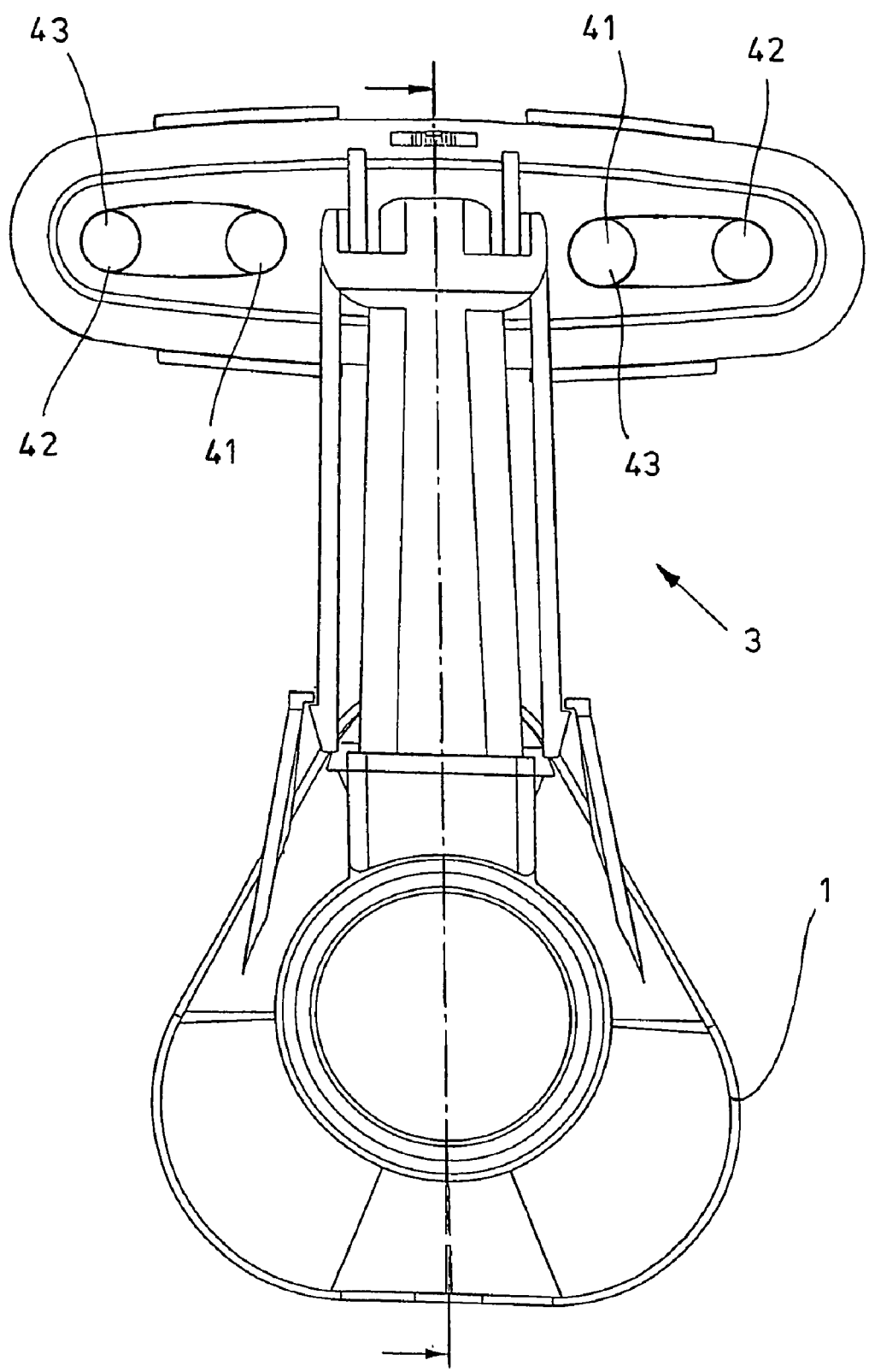
FIG. 12 shows an embodiment with an adjustable discharge opening, in which positionable closure elements are located near the discharge openings.

FIG. 12 shows an embodiment in which at least one group of discharge openings 41, 42, which consists of at least two individual discharge openings 41, 42, is located in the area of the forehead support 3. The discharge openings 41, 42 can be closed by at least one closure element 43, which automatically assumes a certain position, depending on the given spatial position of the patient 7. Depending on the given position of the patient 7, it is thus predetermined that one or more of the discharge openings 41, 42 are closed or open. This makes it possible to open or close different discharge openings 41, 42 when the patient 7 is lying, for example, on his left side, than when he is lying on his right side. It is also possible, depending on whether the patient 7 is in an upright or reclining position, to discharge the respiratory gas through the discharge openings 41, 42 that are the optimum discharge openings under the given current conditions.

Figure 13:
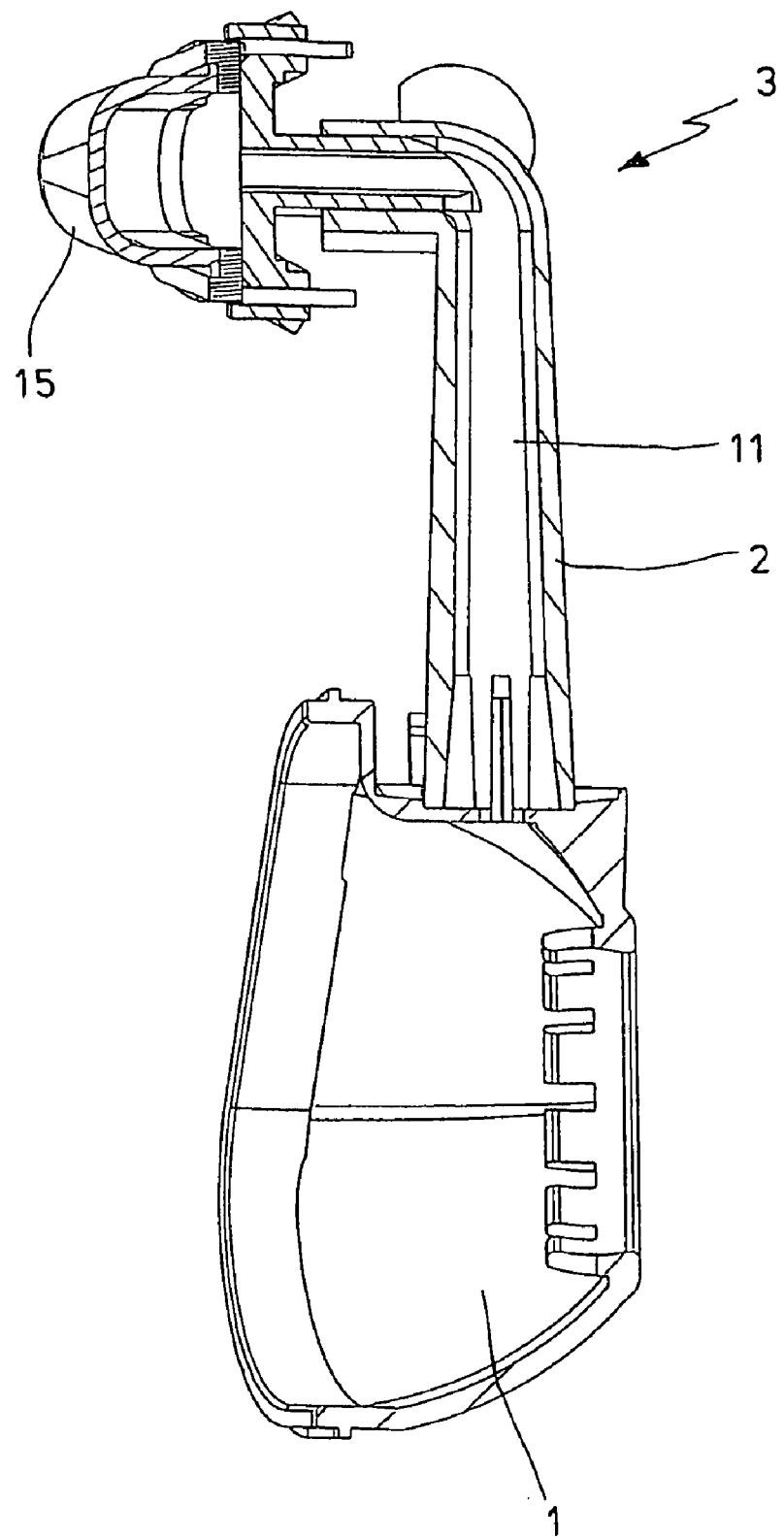
FIG. 13 shows a partially cutaway side view of the embodiment according to FIG. 12.

FIG. 13 shows a partially cutaway side view of the embodiment according to FIG. 12. The exhaled respiratory gas is again fed in the direction of the discharge openings 41, 42 through the cavity 11 of the spacing element 2.

Figure 14:
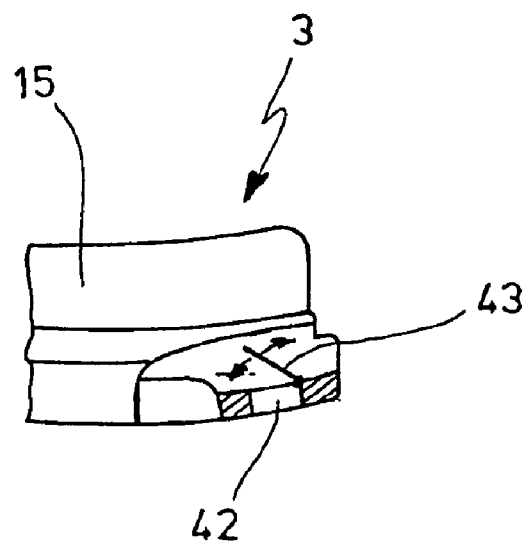
FIG. 14 shows an embodiment with an adjustable closure, in which a baffle that can be set in a desired position is used as the closure element.

FIG. 14 shows an embodiment for realizing the closure element 43 with the use of a movable baffle. Depending on the given spatial position of the forehead support 3, the baffle is open or closed.

Figure 15:
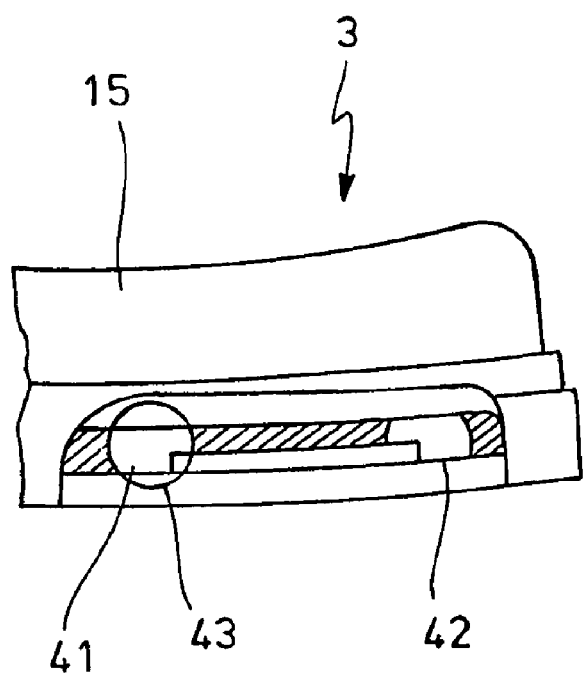
FIG. 15 shows a modification of the embodiment in FIG. 14 with the use of a movable ball.

FIG. 15 shows an embodiment in which the closure element 43 is a movable ball that is arranged in such a way that, depending on the given position of the forehead support 3, one or the other of the discharge openings 41, 42 is closed or neither of the discharge openings 41, 42 is closed.

Figure 16:
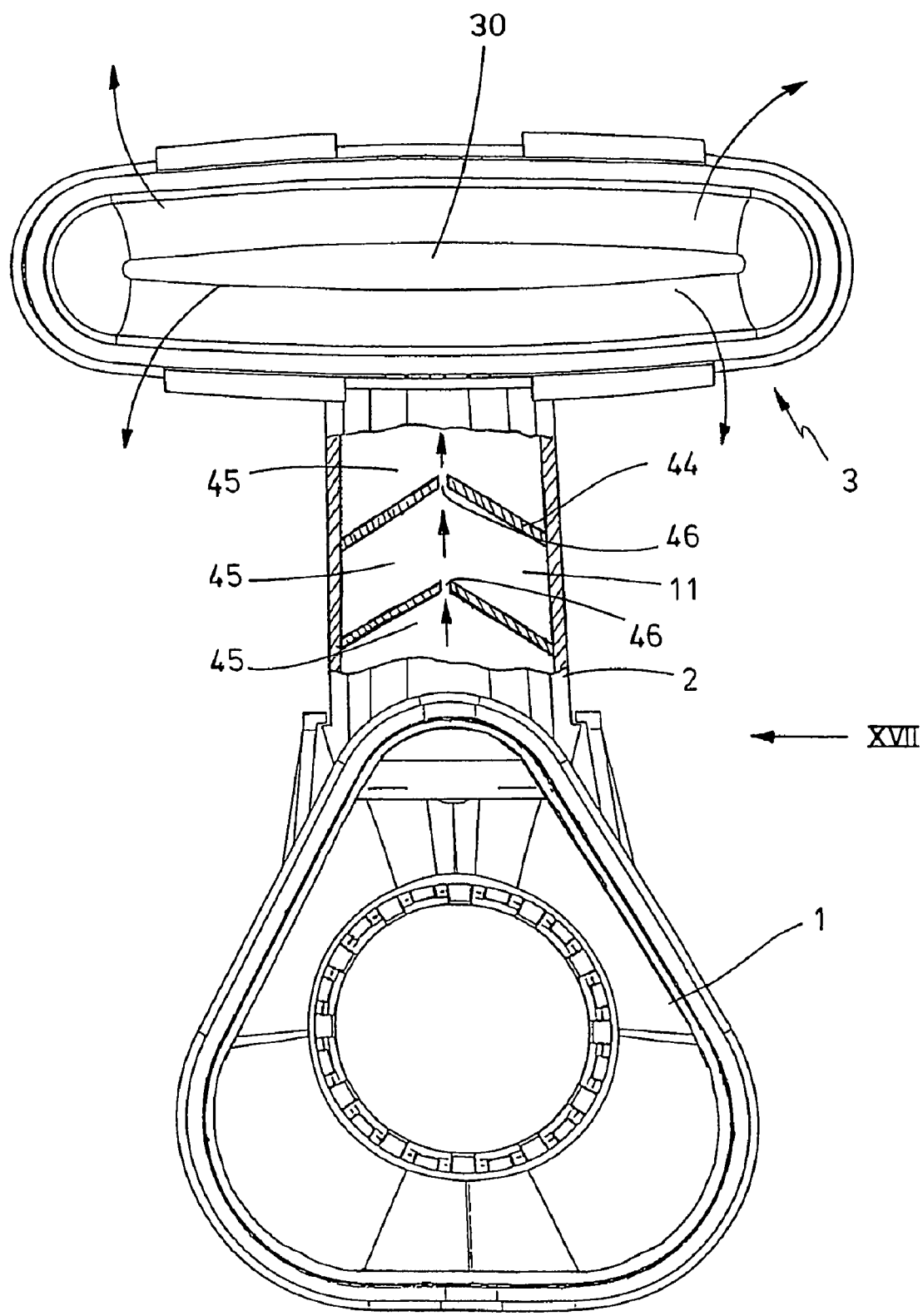
FIG. 16 shows an embodiment with a throttle element in the spacing element to help maintain an internal pressure in the ventilator mask.

FIG. 16 shows an embodiment in which a throttle element 44 is installed in the spacing element 2. The throttle element 44 produces a well-defined discharge resistance for the exhaled respiratory gas and guarantees that a sufficient ventilation pressure can develop in the ventilator mask 1. In the embodiment illustrated in FIG. 16, the throttle element 44 consists of a plurality of lips arranged one behind the other, which separate individual chambers 45 from each other. The chambers 45 are connected with each other only by individual overflow openings 46. In addition to helping produce the necessary ventilation pressure, this arrangement can also improve the level of sound damping.

Figure 17:
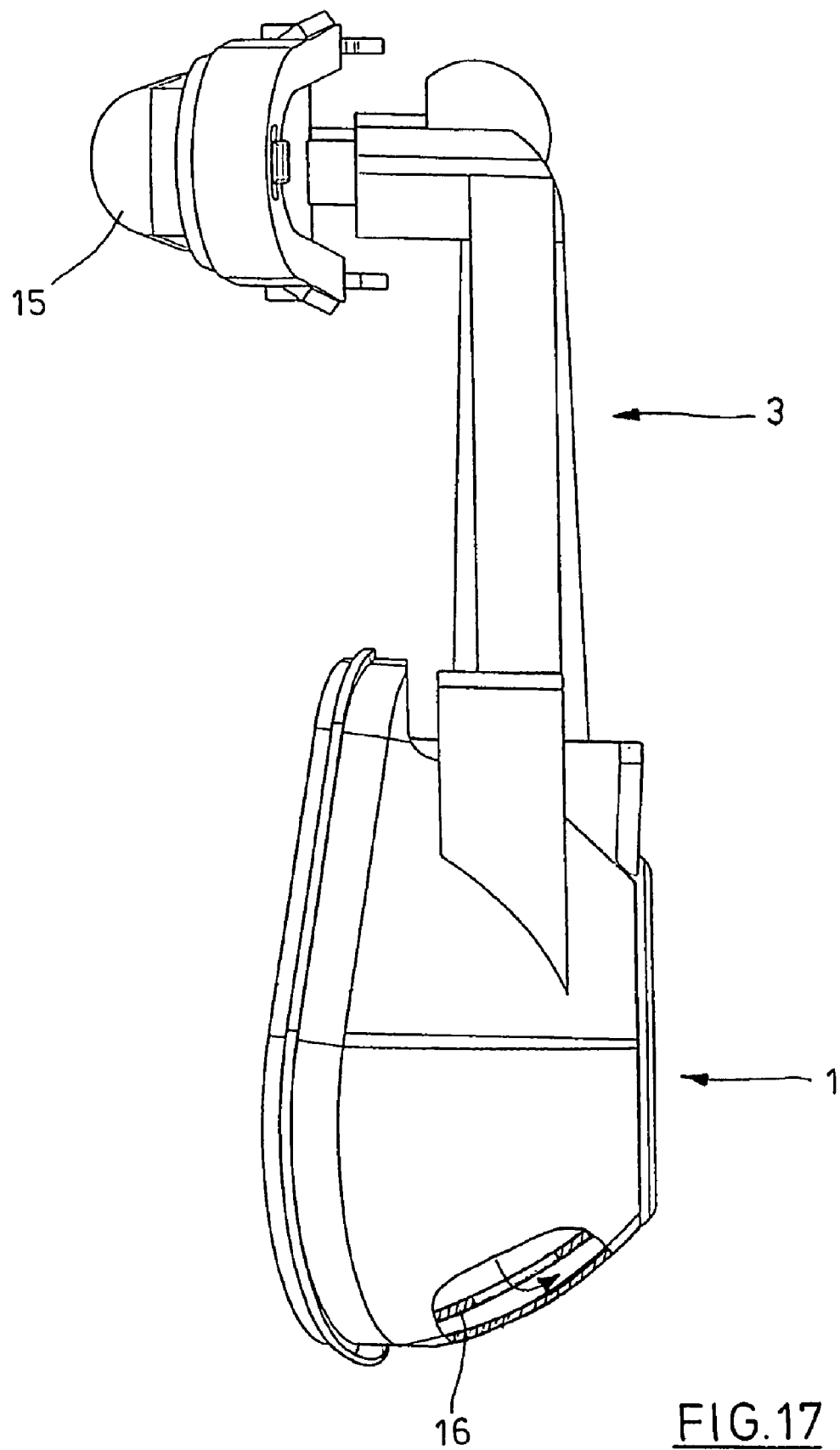
FIG. 17 shows a side view in viewing direction XVII in FIG. 16.

The partially cutaway side view in FIG. 17 shows that, in the embodiment according to FIG. 16, it is also possible to use a double-walled construction with an inner shell 10. In principle, it is possible to use this double-walled construction, which helps achieve optimum elimination of carbon dioxide, in all of the design variants explained here.

Figure 18:
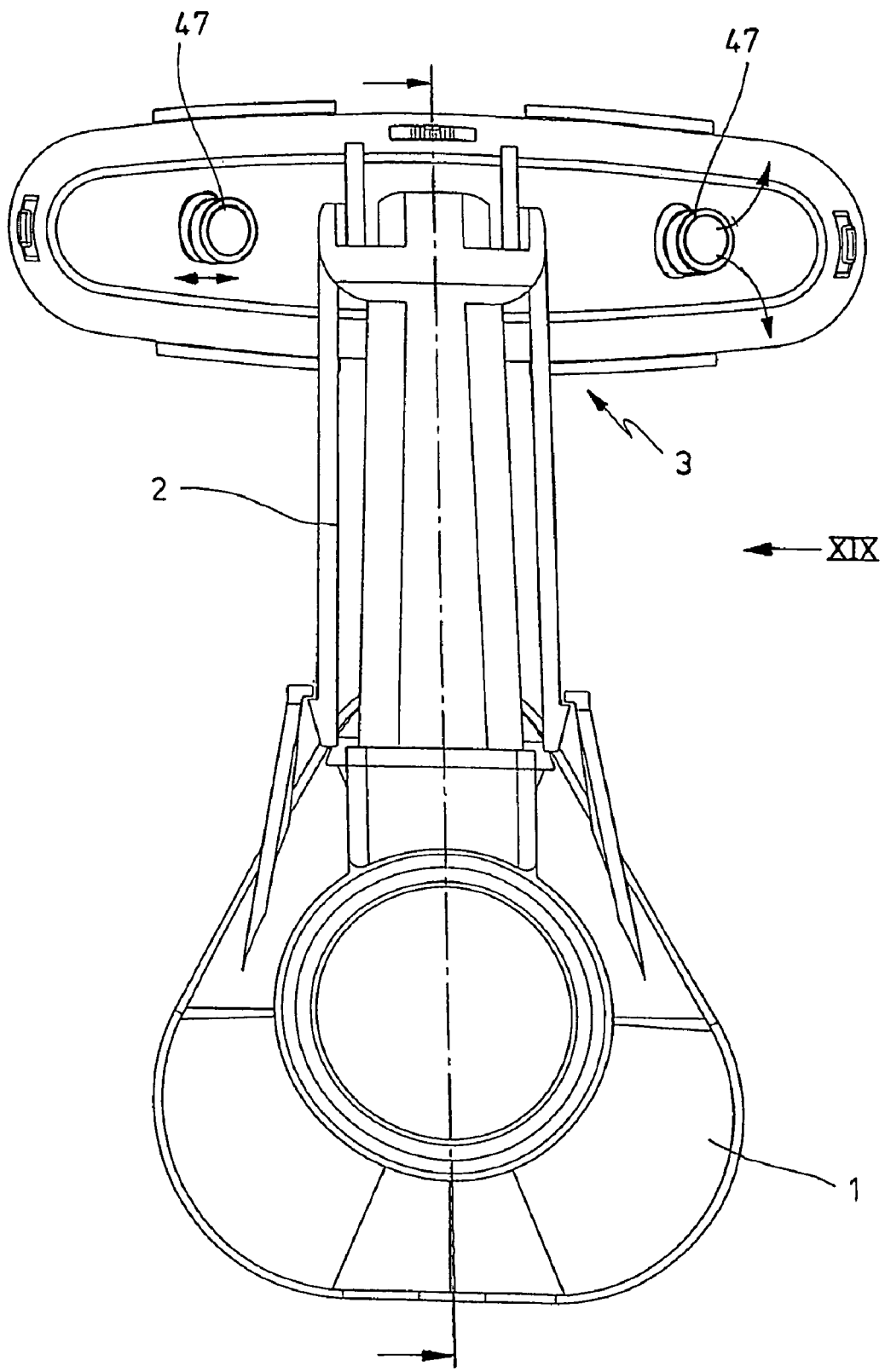
FIG. 18 shows an embodiment with swiveling discharge nozzles.

FIG. 18 shows an embodiment in which movable discharge nozzles 47 are used. The discharge nozzles 47 are installed in the forehead support 3 in a way that allows them to swivel or slide. A desired direction of discharge of the respiratory gas can be preset by moving the discharge nozzles 47 into the corresponding position. For example, when the patient is in the supine position, it is possible to set the discharge nozzles 47 to discharge the respiratory gas directly upward. When the patient is lying on his right side, the discharge nozzles 47 and their openings are turned to the left, and when he is lying on his left side, the discharge nozzles 47 and their openings are turned to the right.

Figure 19:
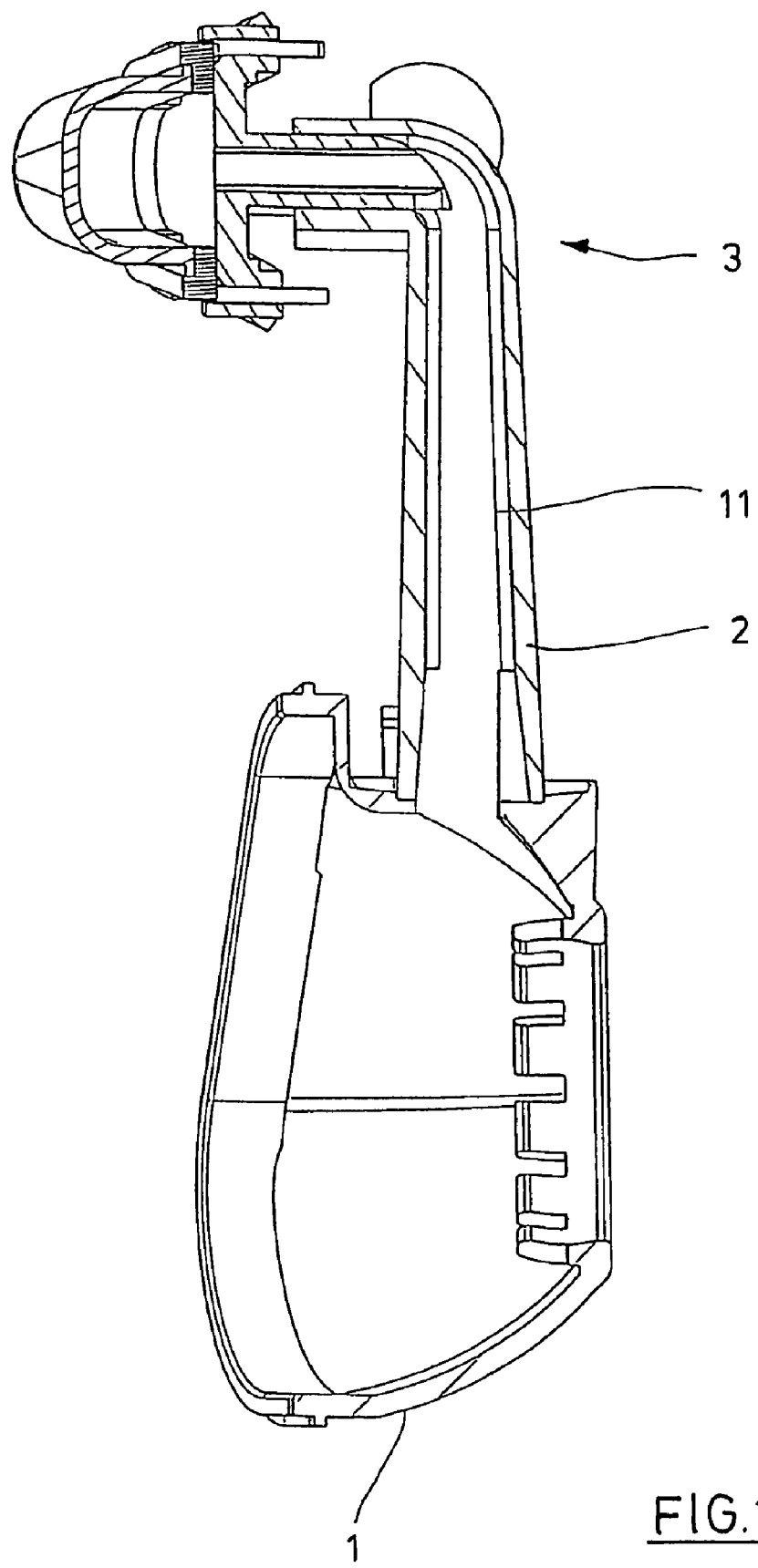
FIG. 19 shows a side view in viewing direction XIX in FIG. 18.

FIG. 19 shows a side view of the embodiment according to FIG. 18. It is also apparent here that exhaled respiratory gas is fed to the discharge nozzles 47 through the cavity 11 of the spacing element 2.

Figure 20:
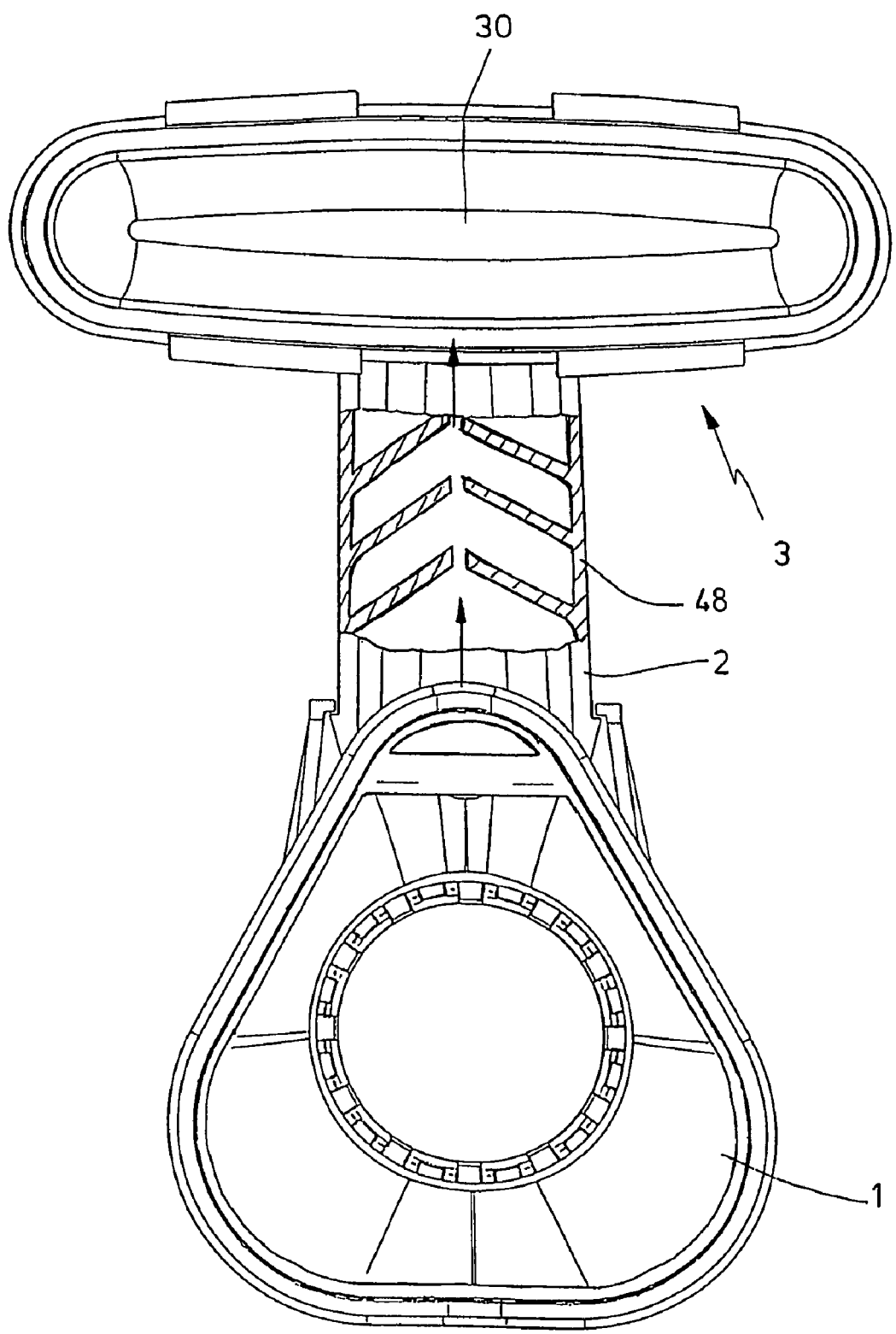
FIG. 20 shows an embodiment with replaceable throttle elements in the spacing element.

In the embodiment in FIG. 20, the throttle element 44 according to FIG. 16 is installed in the spacing element 2 as a removable throttle module 48. This makes it possible to supply a variety of different throttle modules 48, which are inserted in the spacing element 2 according to the individual practical requirements of each case.

Figure 21:
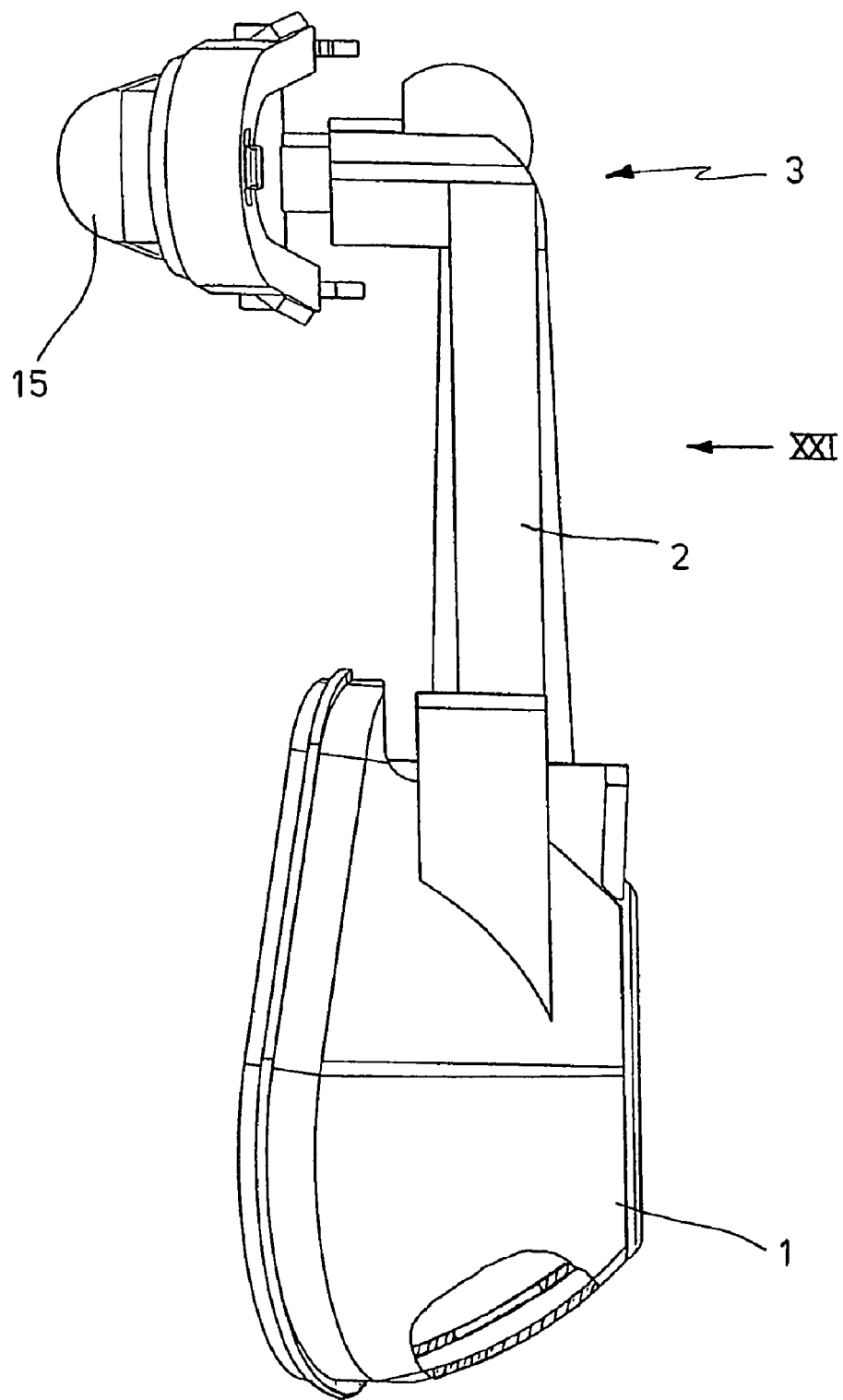
FIG. 21 shows a side view in viewing direction XXI in FIG. 20.

FIG. 21 shows a side view of the ventilator mask 1 with forehead support 3, in which a replaceable throttle module 48 is positioned in the spacing element 2.

Figure 22:
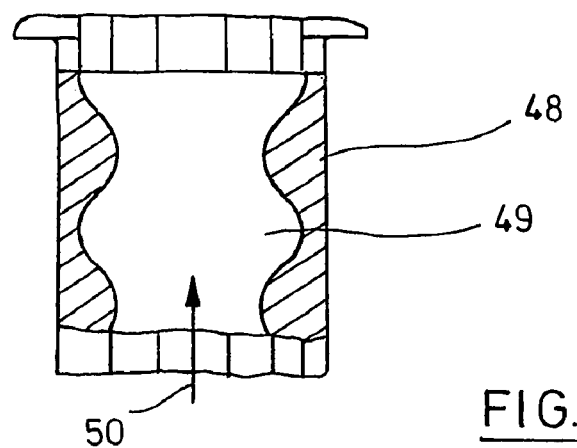
FIG. 22 shows a longitudinal section through a throttle element that is a modification of the throttle element shown in FIG. 20 and has a sinuous flow path.

FIG. 22 shows a design of the throttle module 48, in which a flow path 49 is bounded in such a way by shaped sidewalls that a cross-sectional area that varies in the direction of flow 50 is realized.

Figure 23:
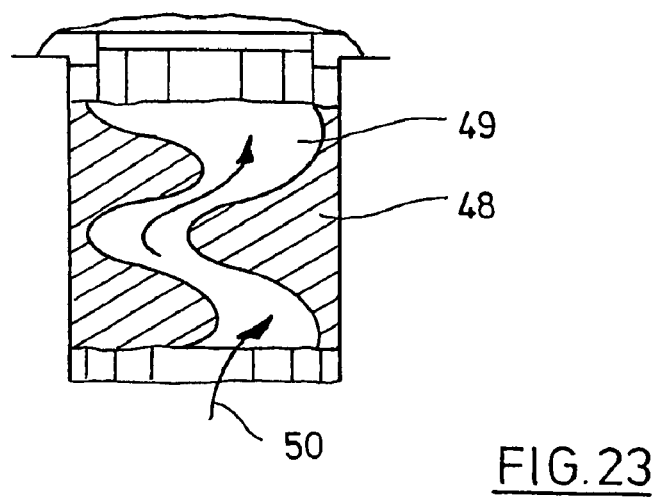
FIG. 23 is a drawing of another modified throttle element.
Figure 24:
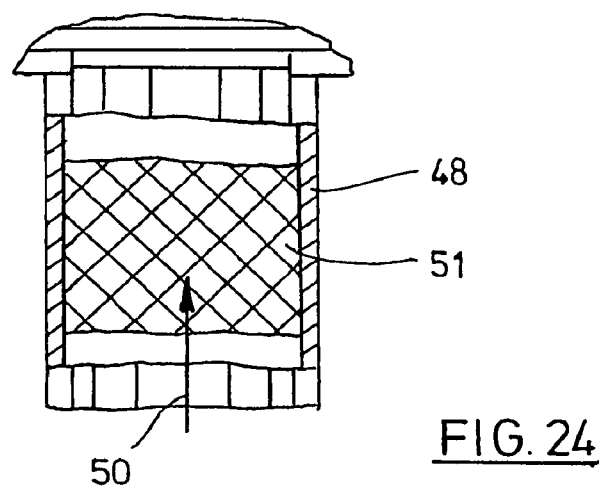
FIG. 24 is a drawing of another throttle element, which consists of porous material.

FIG. 23 shows an embodiment in which the flow in the throttle module 48 follows a winding path 49 with a variable cross-sectional area. In the embodiment in FIG. 24, the throttle module 48 has an insert that consists of a porous material with an internal porosity of up to 4,500 $m^2/g$.

Figure 25:
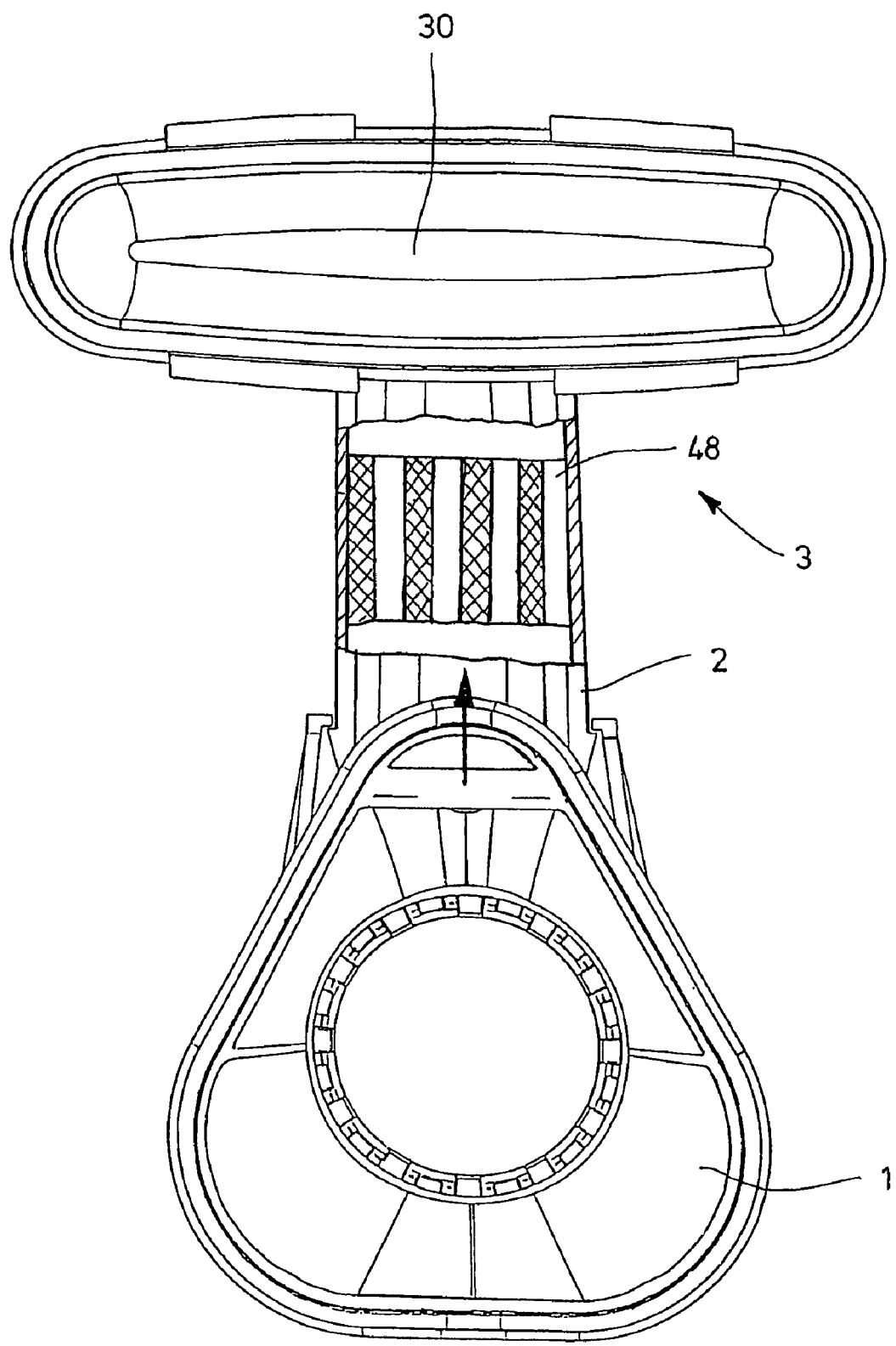
FIG. 25 shows an embodiment that employs another modified throttle element with longitudinal channels.

FIG. 25 shows an embodiment in which the throttle module 48 is designed as a replaceable insert, which, for example, is adapted to specific pressure stages. For example, it is possible to use one insert for a pressure stage of 4-6 mbars, another insert for a pressure range of 6-8 mbars, and other inserts for other pressure stages. The design of the individual throttle modules 48 can be adapted within wide limits to a given practical requirement.

Figure 26:
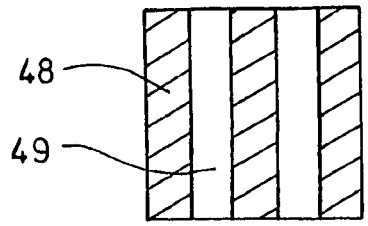
FIG. 26 shows another modification of the throttle element.

FIG. 26 shows an embodiment in which the throttle module 48 has a smaller number of flow paths 49 than the throttle module 48 shown in FIG. 25, although the flow paths 49 have larger cross-sectional areas than those in the embodiment of FIG. 25.

Figure 27:
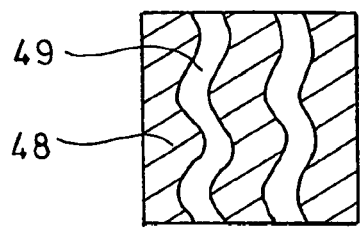
FIG. 27 shows a further modification of the throttle element with a double channel.

In the embodiment shown in FIG. 27, several flow paths 49 with a curved path similar to a serpentine curve extend through the throttle module 48.

Figure 28:
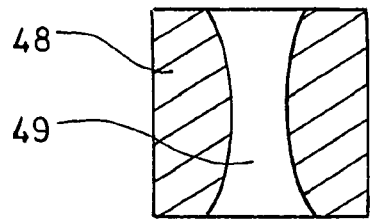
FIG. 28 shows another embodiment of the throttle element with a nozzle-like channel.

In the embodiment shown in FIG. 28, the throttle module 48 has a flow path 49 shaped like a nozzle module, with the nozzle cross section first constricting and then expanding in the direction of flow.

Figure 29:
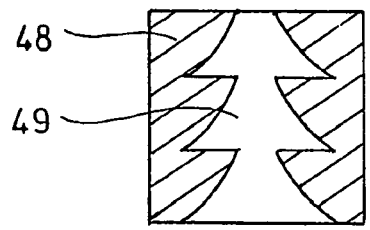
FIG. 29 shows another embodiment of the throttle element.
Figure 30:
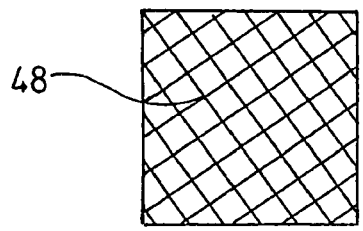
FIG. 30 shows a throttle element in which sintered material is used.

In the embodiment shown in FIG. 29, the flow path 49 follows a course with abrupt changes in cross-sectional area, in which a contour pattern is provided that is similar in shape to the outline of a Christmas tree. The embodiment according to FIG. 30 shows another realization of the throttle module 48 with the use of a porous material, for example, a sintered material.

Figure 31:
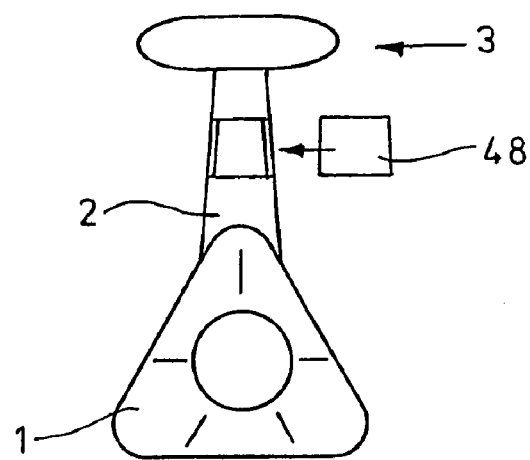
FIG. 31 is a schematic drawing of a ventilator mask with forehead support and spacing element, with the throttle element shown removed from the spacing element.
Figure 32:
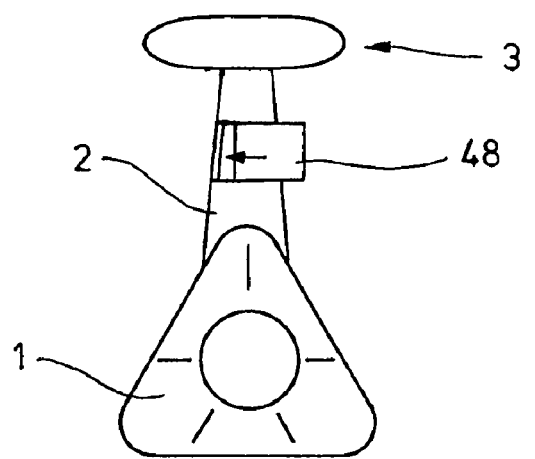
FIG. 32 is a drawing similar to FIG. 31, with the throttle element shown partially inserted.
Figure 33:
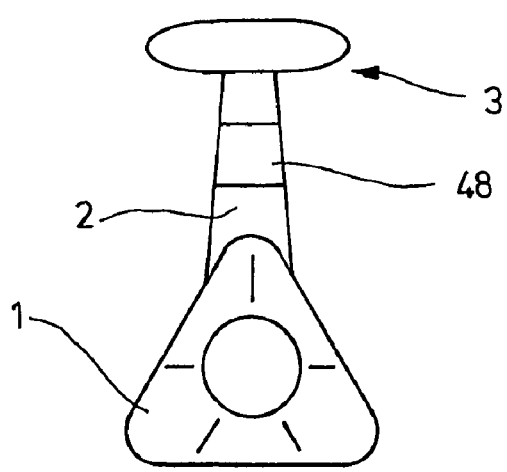
FIG. 33 is a drawing that corresponds to FIG. 31 and FIG. 32, with the throttle element shown completely inserted.

FIG. 31 is a schematic illustration of a throttle module 48 removed from the spacing element 2. In the embodiment shown in FIG. 32, the throttle module 48 was partially inserted in the spacing element 2. The drawing in FIG. 33 shows the throttle module 48 in its final position in the spacing element 2. In particular, it is proposed that the proper insertion of the throttle module 48 in the spacing element 42 be indicated by the generation of an acoustic signal. For example, it is possible, to use locking elements, which produce a clicking sound when the throttle module 48 is fully inserted. The throttle module 48 can be fixed in the spacing element 2 by spring elements, which can be released, for example, by manually squeezing the spring elements.

Figure 34:
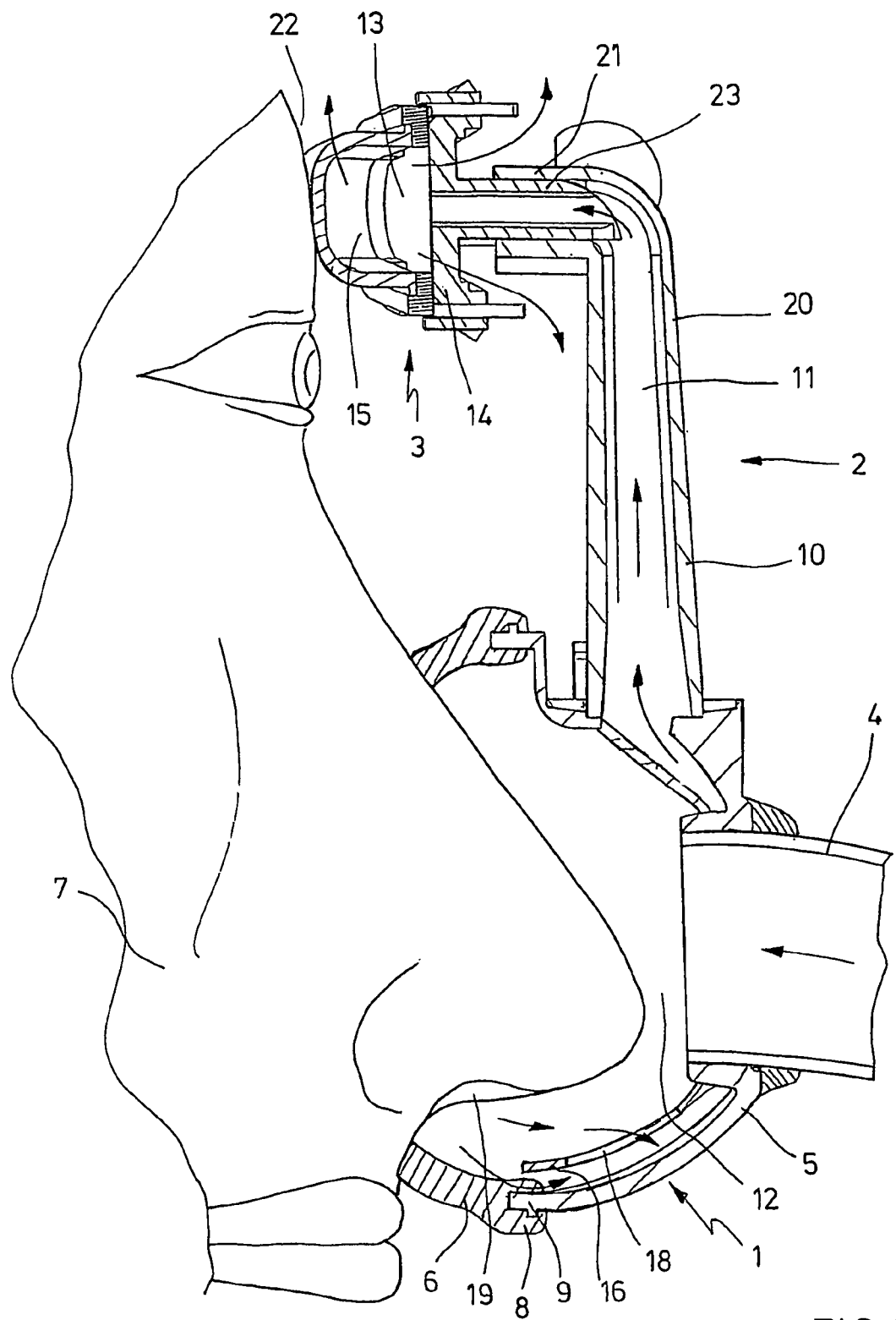
FIG. 34 shows an embodiment that is modified relative to the embodiment in FIG. 1, with flow occurring essentially entirely through the double shell of the ventilator mask.

In the embodiment in FIG. 34, which is a modification of the embodiment in FIG. 1, no passage to the interior space 12 of the ventilator mask 1 is provided vertically below the cavity 11, but rather the entire amount of air exhaled by the patient 7 flows through the opening 18 and into the flow channel 17 between the body 5 of the mask and the inner shell 16. This design further improves the separation of the flow paths for the respiratory gas introduced through the ventilator hose 4 and the respiratory gas exhaled by the patient and prevents thorough mixing of the fresh respiratory gas and the used respiratory gas. This can enhance the effectiveness of the ventilation and reduce the amount of fresh respiratory gas that needs to be supplied.

Figure 35:
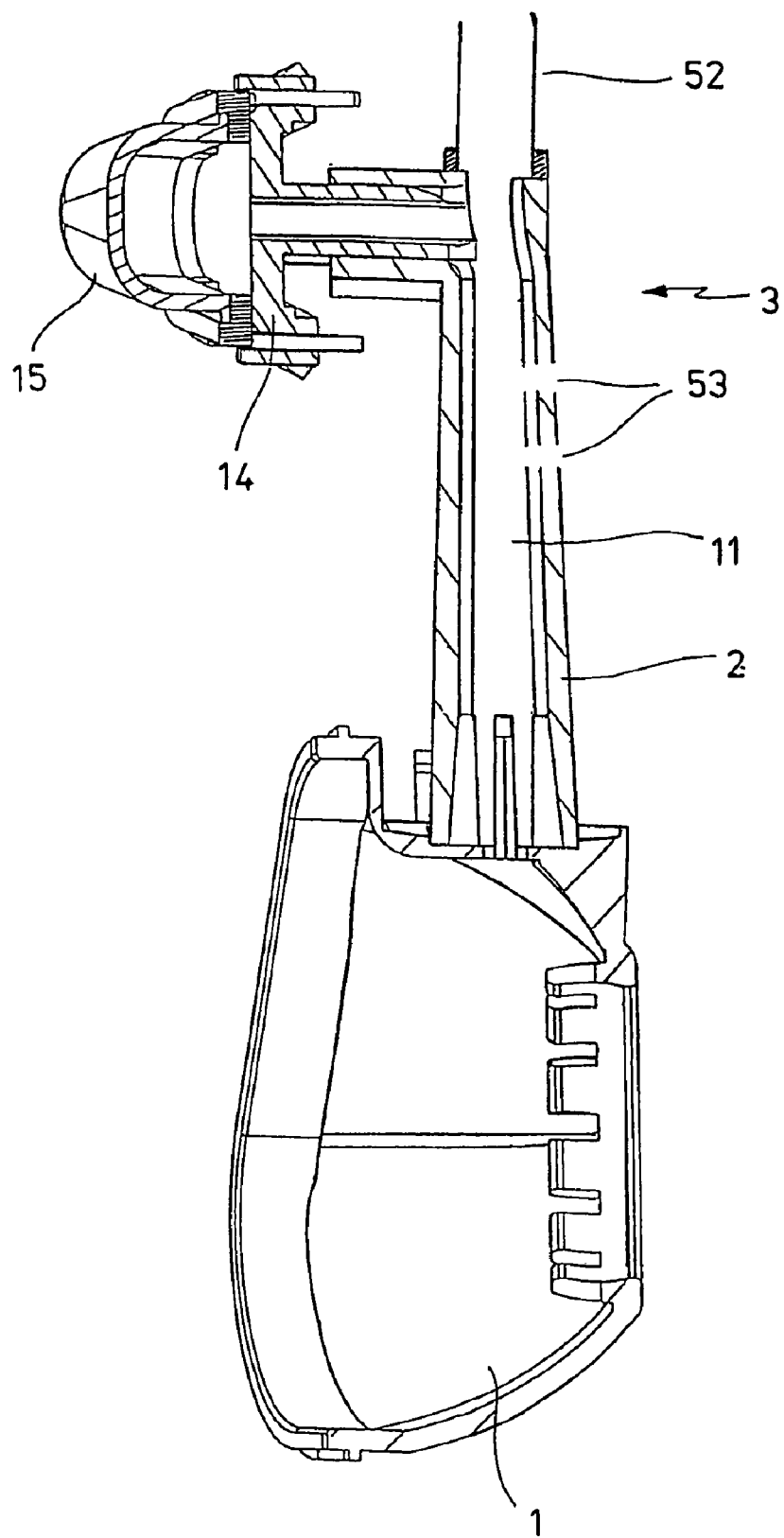
FIG. 35 shows an embodiment that is modified relative to the embodiment in FIG. 13, with a chimney-like discharge element.

FIG. 35 shows a further modified embodiment. In this case, the cavity 11 is not connected with discharge openings in the vicinity of the body 14 of the forehead support 3, but rather the cavity 11 opens into a discharge element 52 that is located basically at a height level above the forehead support 3. The discharge element 52 can be designed, for example, in the form of a connector or a hose. Additional discharge openings 53 can be placed in the spacing element 2.

Figure 36:
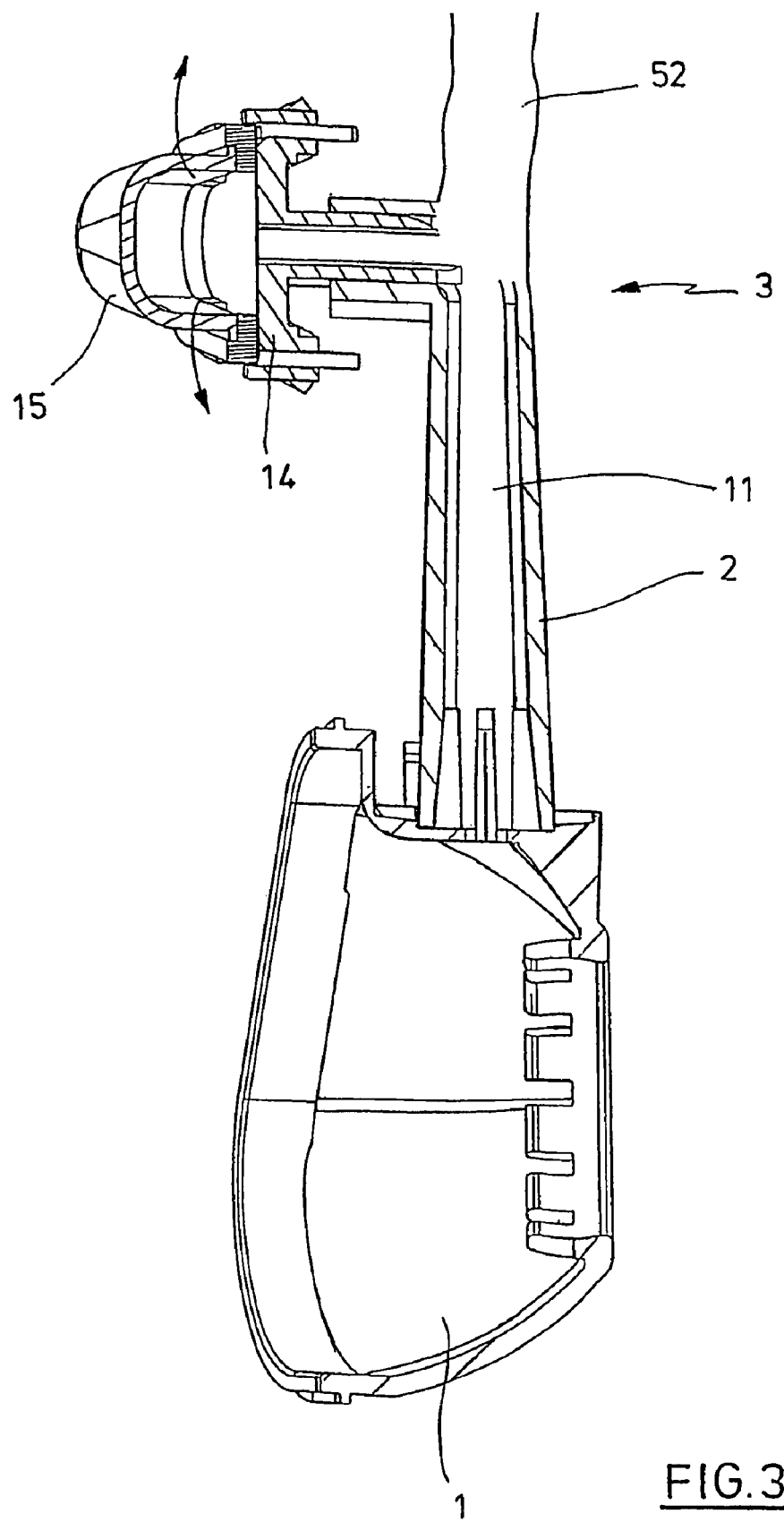
FIG. 36 shows an embodiment that is further modified relative to the embodiment in FIG. 35, with discharge of respiratory gas through both a chimney-like element and through the base of the forehead support.
Figure 37:
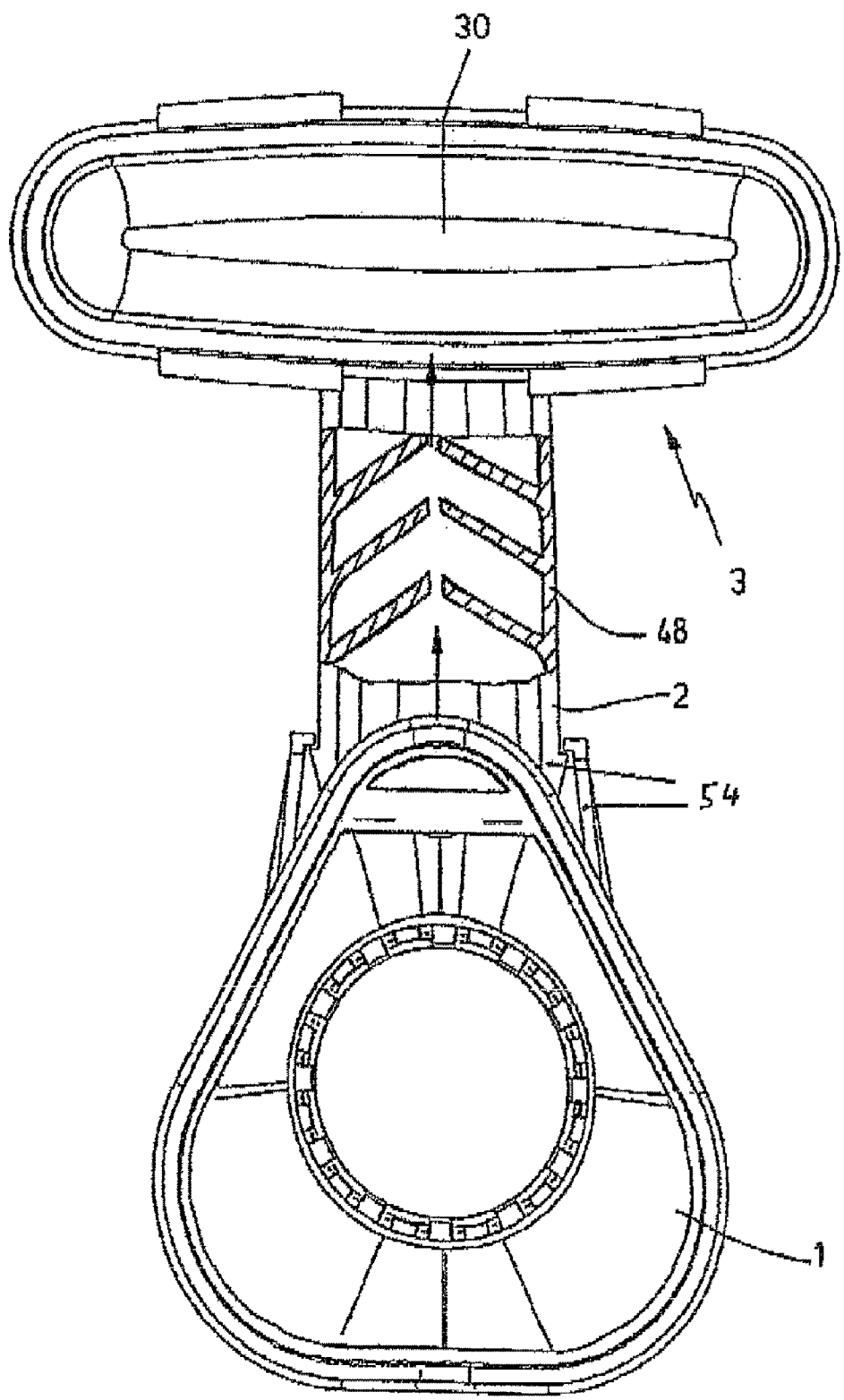
FIG. 37 is a view as in FIG. 20, of an embodiment with a locking mechanism.
Figure 38:
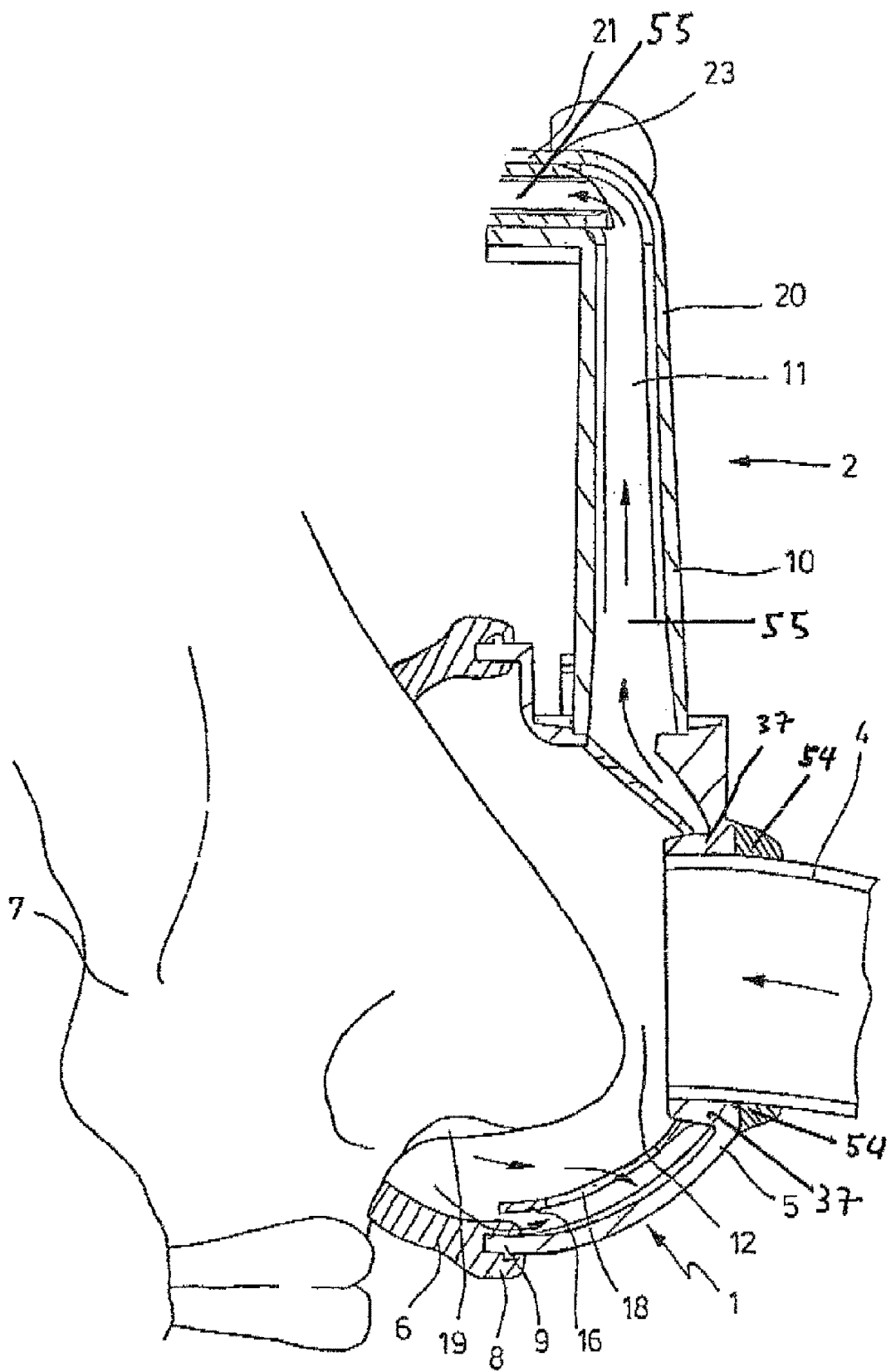
FIG. 38 is a view as in FIG. 34, of an embodiment with a discharge channel.
Figure 39:
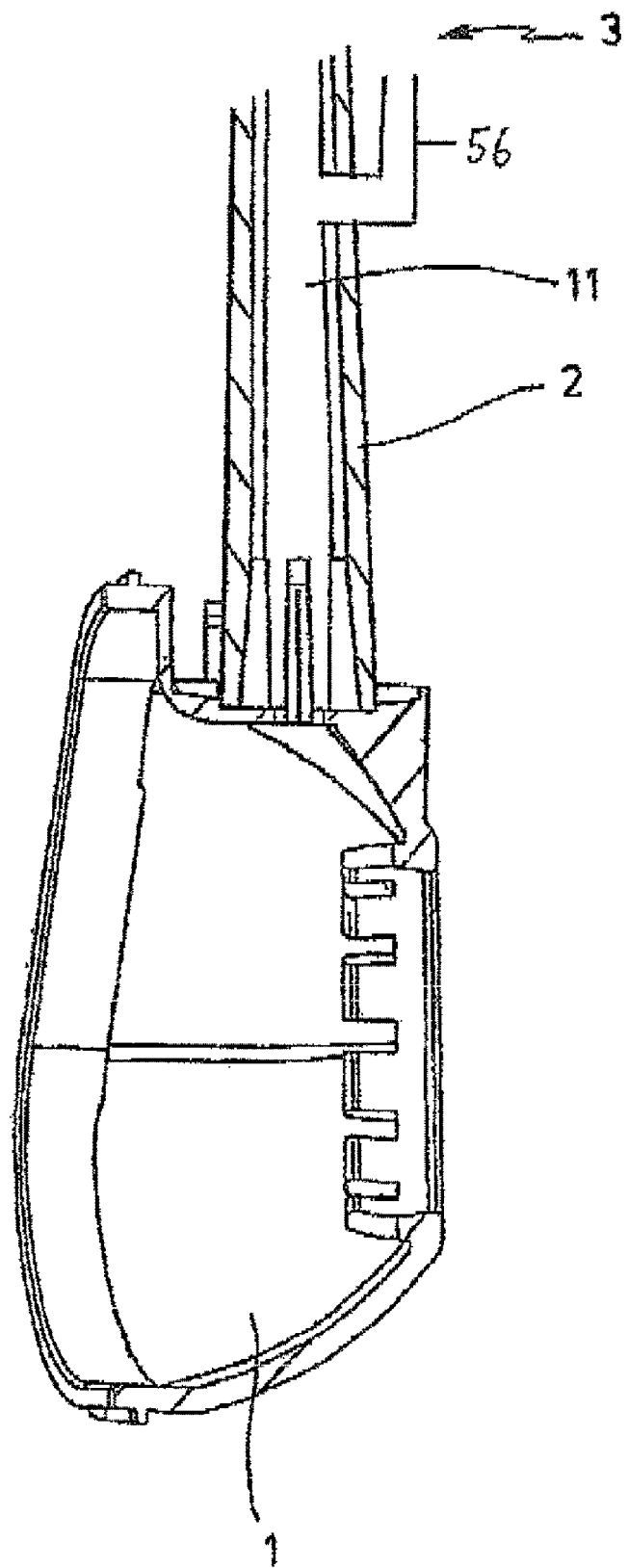
FIG. 39 is a view as in FIG. 36, of an embodiment with an external flow guide element.

FIG. 36 shows an embodiment that is further modified relative to the embodiment in FIG. 35, in which respiratory gas is discharged not only through the chimney-like discharge element 52 but also through the body 14 of the forehead support 3 or the cushion 15 of the forehead support 3. This further increases the discharge area and thus reduces discharge velocities and discharge sounds.

In most of the illustrated embodiments, respiratory gas is discharged from the area of the ventilator mask 1 via a cavity 11 inside the spacing element 2. In principle, it is also possible to place the cavity 11 outside the spacing element 2 but immediately adjacent to the spacing element 2. For example, a hose or other suitable hollow component for conveying the exhaled respiratory gas to the vicinity of the discharge opening provided for this purpose can be arranged parallel to the spacing element 2.

The invention claimed is:

1. A ventilator, comprising a forehead support connected with a ventilator mask, where the ventilator mask is provided with a connection for a ventilator hose, and where the forehead support is coupled with the ventilator mask by a spacing element, wherein the spacing element (2) is provided with a cavity (11), which opens into an interior space (12) of the ventilator mask (1), wherein the ventilator mask has at least two components that have an internal cavity whereby separate flow paths are realized, one of the two components is designed for removing exhaled air, and the other of the components is designed for supplying fresh respiratory gas, wherein the cavity (11) of the spacing element is designed for removing exhaled air in a direction radially away from a body (5) of the mask, wherein the exhaled respiratory gas is fed in a direction of discharge openings (24, 29, 30, 32, 41, 42, 53) through the cavity (11) of the spacing element (2), wherein feeding of respiratory gas occurs via the ventilator hose (4), which is rotatably supported in the body (5) of the mask, and wherein the forehead support (3) is provided with at least one of said discharge openings.

2. A ventilator in accordance with claim 1, wherein the cavity (11) opens into an interior space (13) of the forehead support (3).

3. A ventilator in accordance with claim 1, wherein the spacing element (2) has at least one discharge opening (24).

4. A ventilator in accordance with claim 3, wherein the discharge opening (24) faces away from the patient (7).

5. A ventilator in accordance with claim 1, wherein the discharge opening (29, 30, 32) is arranged to face away from the patient (7).

6. A ventilator in accordance with claim 1, wherein the ventilator mask (1) has a double-walled construction at least in certain areas.

7. A ventilator in accordance with claim 6, wherein the body (5) of the ventilator mask (1) and an inner shell (16) together bound a flow channel (17) that opens into the cavity (11).

8. A ventilator in accordance with claim 7, wherein a coupling part (37) for the ventilator hose (4) extends through the flow channel (17) into a region of the interior space (12) of the ventilator mask (1).

9. A ventilator in accordance with claim 1, wherein an adjustable baffle (25, 35) is installed in an area of at least one of the discharge openings (24, 29, 30, 32) to produce a discharge resistance that can be preset.

10. A ventilator in accordance with claim 9, wherein the baffle (25, 35) is designed to slide.

11. A ventilator in accordance with claim 9, wherein the baffle (25, 35) is designed to rotate.

12. A ventilator in accordance with claim 1, wherein a membrane element (33) is installed in an area of at least one of the discharge openings (24, 29, 30, 32).

13. A ventilator in accordance with claim 1, wherein a slotted silicone insert (34) is installed in an area of at least one of the discharge openings (24, 29, 30, 32).

14. A ventilator in accordance with claim 1, wherein a movable closure element (43) is installed in an area of at least one of the discharge openings (24, 29, 30, 32).

15. A ventilator in accordance with claim 14, wherein the closure element (43) is installed in a way that allows its position to be varied.

16. A ventilator in accordance with claim 14, wherein the closure element (43) is designed as a ball.

17. A ventilator in accordance with claim 1, wherein the cavity (11) of the spacing element is located inside the spacing element (2).

18. A ventilator in accordance with claim 1, wherein the cavity (11) of the spacing element is located in a flow guide element outside the spacing element (2).

19. A ventilator in accordance with claim 1, wherein the ventilator mask (1) comprises at least two detachably connected components.

20. A ventilator in accordance with claim 19, wherein the two or more components are connected with one another by a manually releasable locking mechanism.

21. A ventilator in accordance with claim 1, wherein at least one of the components is hollow and is designed for removing exhaled air.

22. A ventilator, comprising a ventilator mask and in which the ventilator mask is provided with a connection for a ventilator hose, wherein the ventilator mask (1) consists of at least three detachably connected components, of which at least two components are connected with one another by a manually releasable locking mechanism, and one of the components is designed for removing exhaled air, and the other component is designed for supplying fresh respiratory gas, wherein at least two of the components have an internal cavity, and one of the components is designed for removing exhaled air, and the other component is designed for supplying fresh respiratory gas, wherein a cavity (11) of a spacing element is designed for removing exhaled air in a direction radially away from a body (5) of the mask, wherein the exhaled respiratory gas is fed in a direction of discharge openings (24, 29, 30, 32, 41, 42, 53) through the cavity (11) of the spacing element (2), wherein feeding of respiratory gas occurs via the ventilator hose (4), which is rotatably supported in the body (5) of the mask, and wherein a forehead support (3) is provided with at least one of said discharge openings.

23. A ventilator in accordance with claim 22, wherein at least two of the components have an internal cavity and that in at least one operating state, a higher average concentration of carbon dioxide is present in one of the hollow components than in the area of the other component.

24. A ventilator, comprising a ventilator mask and in which the ventilator mask is provided with a connection for a ventilator hose, wherein the ventilator mask (1) has at least three interconnected openings, where at least one of the openings opens into a cavity, and where at least one of the openings is designed for removing exhaled air, and one of the other openings is designed for supplying fresh respiratory gas, wherein at least one of the openings opens into a cavity and is designed for removing exhaled air in a direction radially away from a body of the mask, and one of the other openings is designed for supplying fresh respiratory gas, wherein the exhaled respiratory gas is fed in a direction of discharge openings (24, 29, 30, 32, 41, 42, 53) through a cavity (11) of a spacing element (2), wherein feeding of respiratory gas occurs via the ventilator hose (4), which is rotatably supported in the body (5) of the mask, and wherein a forehead support (3) is provided with at least one of said discharge openings.

25. A ventilator in accordance with claim 24, wherein at least one of the openings has an internal cavity, and where this opening is designed for removing exhaled air above the eye level of the patient, while one of the other openings is designed for supplying fresh respiratory gas.

26. A ventilator in accordance with claim 24, wherein at least one of the openings opens into a cavity, and where this opening is designed for discharging exhaled air to a point far from the patient's face, while one of the other openings is designed for supplying fresh respiratory gas.

27. A ventilator in accordance with claim 1, wherein a discharge channel for creating an exhalation system extends along at least certain parts of the forehead support (3).

28. A ventilator in accordance with claim 1, wherein a flow path into the ventilator mask for an air flow coming from a compressed gas source is provided and where a discharge channel for discharging the exhaled air is provided, such that the discharge channel extends at an angle of 45.degree. to 135.degree. relative to a plane that is defined by the perpendicular plane of the cross-section of a inlet for the respiratory gas supply.

29. A ventilator in accordance with claim 1, wherein a cavity located in the forehead support (3) is connected by at least one connecting passage with an interior space of the ventilator mask (1) and at least one discharge opening.

* * * * *